(12) United States Patent
Wanker et al.

(10) Patent No.: US 7,595,199 B1
(45) Date of Patent: Sep. 29, 2009

(54) METHOD OF DETECTING AMYLOID-LIKE FIBRILS OR PROTEIN AGGREGATES

(75) Inventors: Erich Wanker, Berlin (DE); Hans Lehrach, Berlin (DE); Eberhard Scherzinger, Berlin (DE); Gillian Bates, London (GB)

(73) Assignee: Max-Planck-Gesellschaft zur Förderung der Wissenchaften e.V., Berlin (DE)

( * ) Notice: Subject to any disclaimer, the term of this patent is extended or adjusted under 35 U.S.C. 154(b) by 0 days.

(21) Appl. No.: 09/485,005

(22) PCT Filed: Jul. 31, 1998

(86) PCT No.: PCT/EP98/04810

§ 371 (c)(1),
(2), (4) Date: Sep. 11, 2000

(87) PCT Pub. No.: WO99/06838

PCT Pub. Date: Feb. 11, 1999

(51) Int. Cl.
*G01N 1/18* (2006.01)
(52) U.S. Cl. ............... 436/177; 436/15; 436/17; 436/161; 436/175; 436/178; 436/514; 436/288.6; 436/962; 435/2; 435/7.1; 435/7.92; 435/12; 435/287.2; 530/350; 514/12
(58) Field of Classification Search ............... 435/2, 435/7.1, 7.71, 7.92, 7.93, 7.94, 12, 287.2, 435/287.7, 288.6, 962; 436/177–179, 514, 436/530, 538, 539, 541, 546, 17, 161, 175, 436/520, 15; 514/12; 530/387.1, 387.9, 530/350
See application file for complete search history.

(56) References Cited

U.S. PATENT DOCUMENTS

| | | | | |
|---|---|---|---|---|
| 4,094,775 A | * | 6/1978 | Mueller | 210/646 |
| 5,234,814 A | | 8/1993 | Card et al. | 435/7.21 |
| 5,723,301 A | | 3/1998 | Burke et al. | 435/7.1 |
| 5,935,927 A | * | 8/1999 | Vitck et al. | 514/21 |
| 6,235,879 B1 | * | 5/2001 | Kalchman et al. | 530/350 |
| 6,365,414 B1 | * | 4/2002 | Tanzi et al. | 436/86 |
| 6,428,785 B1 | * | 8/2002 | Gokcen | 424/94.2 |
| 6,743,432 B1 | * | 6/2004 | Yanai et al. | 424/400 |

FOREIGN PATENT DOCUMENTS

| | | | |
|---|---|---|---|
| EP | 0 206302 A2 | 12/1986 | |
| EP | 0 293 249 A1 | 11/1988 | |
| EP | 0 854 364 A1 | 7/1998 | |
| WO | WO95/29243 | 2/1995 | |
| WO | WO96/12544 | 2/1996 | |
| WO | WO96/28471 | 9/1996 | |
| WO | WO97/17445 | 5/1997 | |
| WO | WO 97/18825 | * 5/1997 | 436/177 |
| WO | WO 99/06545 | 2/1999 | |

OTHER PUBLICATIONS

Mignotte et al. (Mitochondrial DNA-Binding Proteins that bind preferentially to Supercoiled Molecules containing the D-Loop Region of Xenopus Laevis mtDNA, Biochemical and Biophysical Research Communications, Nov. 30, 1983).*

Notario et al. (Changes in the membrane proteins of blood cells in the course of embryonal megaloerythropoiesis in relation to hemoglobin maturation) Archivio per le scienze mediche, 135 (1): 1-8 (Jan.-Mar. 1978) Abstract).*

Selkoe et al. Alzheimer's Disease: Insolubility of Partially Purified Helical Filaments in Sodium Dodecyl Sulfate and Urea; Science 215: 1243-1245 (1982).*

Kisilevsky et al., "Arresting amyloidosis in vivo using small-molecule anionic sulphonates or sulphates: implications for Alzheimer's disease", (Feb. 1995), pp. 143-148, *Nature Medicine*, vol. 1, No. 2.

Trottler et al., "Polyglutamine expansion as a pathological epitope in Huntington's disease and four dominant cerebellar ataxias", (Nov. 23, 1985), pp. 403-406, *Nature* vol. 378.

Gutekunst et al., "Identification and localization of huntingtin in brain and human lymphoblastoid cell lines with anti-fusion protein antibodies", (Sep. 1995), pp. 8710-8714, *Pro. Natl. Acad. Sci. USA* vol. 92 Neurobiology.

M.F. Perutz, "Glutamine repeats and inherited neurodegenerative diseases: molecular aspects", (1996) pp. 848-858, *MRC Laboratory of Molecular Biology*.

Mangiarini et al., "Exon 1 of the *HD* gene with an expanded CAG repeat is sufficient to cause a progressive neurological phenotype in transgenic mice", (Nov. 1, 1996), pp. 493-506, *Cell*, vol. 87.

Stott et al., "Incorporation of glutamine repeats makes protein oligomerize: implications for neurodegenerative diseases", (Jul. 1995), pp. 6509-6513, *Pro. Natl. Acad. Sci. USA*, vol. 92, Biochemistry.

Merlini et al., "Interaction of the anthracycline 4'-iodo-4'-deoxydoxorubicin with anyloid fibrils: Inhibition of amyloidogenesis", (Mar. 1995), pp. 2959-2963, *Proc. Natl. Acad. Sci. USA*, vol. 92, Medical Sciences.

Scherzinger, et al., "Huntingtin-encoded polyglutamine expansions form amyloid-like protein aggregates in vitro and in vivo", (Aug. 8, 1997), pp. 549-558, *Cell*, vol. 90.

(Continued)

*Primary Examiner*—Gailene R Gabel
(74) *Attorney, Agent, or Firm*—Wolf, Greenfield & Sacks, P.C.

(57) ABSTRACT

The present invention relates to methods of detecting the presence of detergent- or urea-insoluble amyloid-like fibrils or protein aggregates on filters. Preferably, said fibrils or aggregates are indicative of a disease, preferably of a neurodegenerative disease such as Alzheimer's disease or Huntington's disease. In addition, the present invention relates to inhibitors identified by the method of the invention, to pharmaceutical compositions comprising said inhibitors and to diagnostic compositions useful for the investigation of said amyloid-like fibrils or aggregates.

33 Claims, 11 Drawing Sheets

OTHER PUBLICATIONS

Figure 1A:
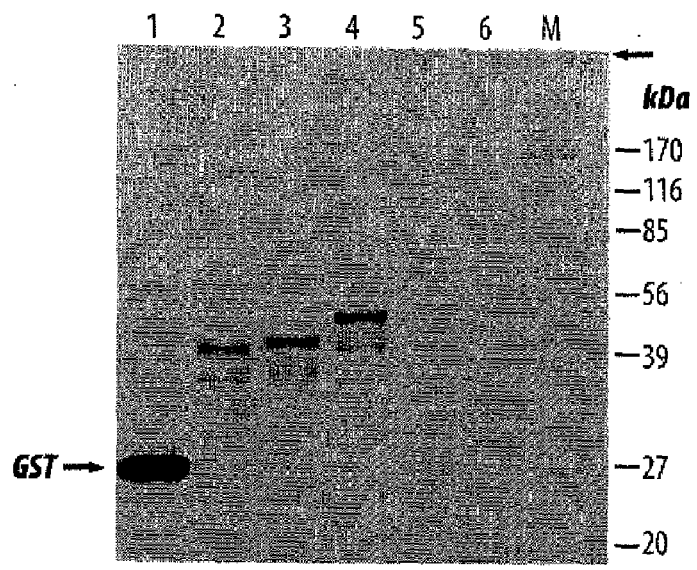

Davies et al., "Formation of neuronal intranuclear inclusions underlies the neurological dysfunction in mice transgenic for the HD mutation", (Aug. 8, 1997), pp. 537-548, *Cell*, vol. 90.

Derwent, "Nucleic acid fragments associated with spinocerebellar ataxis type 2-contain increased number of CAG repeat region compared to normal gene", (May 7, 1998), XP-002101183.

Tateishe et al., "Removal of causative agent of creutzefeldt-jakob disease (CJD) through membrane filtration method", (1993), pp. 357-362, *Membrane*, 18(6).

Bates, G.P. et al., Transgenic models of Huntington's disease. Hum Mol Genet. 1997;6(10):1633-7.

Becher, M.W. et al., Intranuclear neuronal inclusions in Huntington's disease and dentatorubral and pallidoluysian atrophy: correlation between the density of inclusions and IT15 CAG triplet repeat length. Neurobiol Dis. Apr. 1998;4(6):387-97.

Beyreuther, K. et al., Alzheimer's disease. Tangle disentanglement. Nature. Oct. 10, 1996;383(6600):476-7.

Booth, D.R. et al., Instability, unfolding and aggregation of human lysozyme variants underlying amyloid fibrillogenesis. Nature. Feb. 27, 1997;385(6619):787-93.

Burke, J.R. et al., Huntingtin and DRPLA proteins selectively interact with the enzyme GAPDH. Nat Med. Mar. 1996;2(3):347-50.

Caputo, C.B. et al., Amyloid-like properties of a synthetic peptide corresponding to the carboxy terminus of beta-amyloid protein precursor. Arch Biochem Biophys. Jan. 1992;292(1):199-205.

Caughey, B. and Chesebro, B. Prion protein and the transmissible spongiform encephalopaties. Trends Cell Biol. 1997; 7: 56-62.

De Rooij, K.E. et al., Subcellular localization of the Huntington's disease gene product in cell lines by immunofluorescence and biochemical subcellular fractionation. Hum Mol Genet. Aug. 1996;5(8):1093-9.

Difiglia, M. et al., Aggregation of huntingtin in neuronal intranuclear inclusions and dystrophic neurites in brain. Science. Sep. 26, 1997;277(5334):1990-3.

Difiglia, M. et al., Huntingtin is a cytoplasmic protein associated with vesicles in human and rat brain neurons. Neuron. May 1995;14(5):1075-81.

Duyao, M.P. et al., Inactivation of the mouse Huntington's disease gene homolog Hdh. Science. Jul. 21, 1995;269(5222):407-10.

Georgalis, Y. et al., Huntingtin aggregation monitored by dynamic light scattering. Proc Natl Acad Sci U S A. May 26, 1998;95(11):6118-21.

Glenner, G.G. Amyloid deposits and amyloidosis. The beta-fibrilloses (first of two parts). N Engl J Med. Jun. 5, 1980;302(23):1283-92 and 1333-1343.

Goldberg, Y.P. et al., Cleavage of huntingtin by apopain, a proapoptotic cysteine protease, is modulated by the polyglutamine tract. Nat Genet. Aug. 1996;13(4):442-9.

HDCRG. A novel gene containing a trinucleotide repeat that is expanded and unstable on Huntington's disease chromosomes. The Huntington's Disease Collaborative Research Group. Cell. Mar. 26, 1993;72(6):971-83.

Holmberg, M. et al., Spinocerebellar ataxia type 7 (SCA7): a neurodegenerative disorder with neuronal intranuclear inclusions. Hum Mol Genet. May 1998;7(5):913-8.

Hoogeveen, A.T. et al., Characterization and localization of the Huntington disease gene product. Hum Mol Genet. Dec. 1993;2(12):2069-73.

Igarashi, S. et al., Suppression of aggregate formation and apoptosis by transglutaminase inhibitors in cells expressing truncated DRPLA protein with an expanded polyglutamine stretch. Nat Genet. Feb. 1998;18(2):111-7.

Ikeda, H. et al., Expanded polyglutamine in the Machado-Joseph disease protein induces cell death in vitro and in vivo. Nat Genet. Jun. 1996;13(2):196-202.

Jarrett, J.T. and Lansbury, P.T. Seeding "one-dimensional crystallization" of amyloid: a pathogenic mechanism in Alzheimer's disease and scrapie? Cell. Jun. 18, 1993;73(6):1055-8.

Kalchman, M.A. et al., HIP1, a human homologue of S. cerevisiae Sla2p, interacts with membrane-associated huntingtin in the brain. Nat Genet. May 1997;16(1):44-53.

Kalchman, M.A. et al., Huntingtin is ubiquitinated and interacts with a specific ubiquitin-conjugating enzyme. J Biol Chem. Aug. 9, 1996;271(32):19385-94.

Li, X.-J. et al., A huntingtin-associated protein enriched in brain with implications for pathology. Nature. Nov. 23, 1995;378(6555):398-402.

Lim, K. et al., Three-dimensional structure of Schistosoma japonicum glutathione S-transferase fused with a six-amino acid conserved neutralizing epitope of gp41 from HIV. Protein Sci. Dec. 1994;3(12):2233-44.

Matilla, A. et al., The cerebellar leucine-rich acidic nuclear protein interacts with ataxin-1. Nature. Oct. 30, 1997;389(6654):974-8. Erratum in: Nature Feb. 19, 1998;391(6669):818.

Onodera, O. et al., Toxicity of expanded polyglutamine-domain proteins in *Escherichia coli*. FEBS Lett. Dec. 9, 1996;399(1-2):135-9.

Paulson, H.L. et al., Intranuclear inclusions of expanded polyglutamine protein in spinocerebellar ataxia type 3. Neuron. Aug. 1997;19(2):333-44.

Perutz, M.F. et al., Glutamine repeats as polar zippers: their possible role in inherited neurodegenerative diseases. Proc Natl Acad Sci U S A. Jun. 7, 1994;91(12):5355-8.

Portera-Cailliau, C. et al., Evidence for apoptotic cell death in Huntington disease and excitotoxic animal models. J Neurosci. May 1995;15(5 Pt 2):3775-87.

Prusiner, S.B. et al., Scrapie prions aggregate to form amyloid-like birefringent rods. Cell. Dec. 1983;35(2 Pt 1):349-58.

Roizin, L. et al., Neuronal nuclear-cytoplasmic changer in Huntington's chorea. J. Neurol. Sci. 1983; 61: 37-47.

Roos, R.A.C. et al., Nuclear membrane indentations in Huntington's chorea. J Neurol Sci. Sep. 1983;61(1):37-47.

Ross, C.A. When more is less: pathogenesis of glutamine repeat neurodegenerative diseases. Neuron. Sep. 1995;15(3):493-6.

Rubinsztein, D.C. et al., Phenotypic characterization of individuals with 30-40 CAG repeats in the Huntington disease (HD) gene reveals HD cases with 36 repeats and apparently normal elderly individuals with 36-39 repeats. Am J Hum Genet. Jul. 1996;59(1):16-22.

Sathasivam, K. et al., Identification of an HD patient with a (CAG)180 repeat expansion and the propagation of highly expanded CAG repeats in lambda phage. Hum Genet. 1997 May;99(5):692-5.

Schatz, P.J. Use of peptide libraries to map the substrate specificity of a peptide-modifying enzyme: a 13 residue consensus peptide specifies biotinylation in *Escherichia coli*. Biotechnology (N Y). Oct. 1993;11(10):1138-43.

Scherzinger, E. et al., Huntingtin-encoded polyglutamine expansions form amyloid-like protein aggregates in vitro and in vivo. Cell. Aug. 8, 1997;90(3):549-58.

Sharp, A.H. et al., Widespread expression of Huntington's disease gene (IT15) protein product. Neuron. May 1995;14(5):1065-74.

Sittler, A. et al., Alternative splicing of exon 14 determines nuclear or cytoplasmic localisation of fmr1 protein isoforms. Hum Mol Genet. Jan. 1996;5(1):95-102.

Sittler, A. et al., SH3GL3 associates with the Huntingtin exon 1 protein and promotes the formation of polygln-containing protein aggregates. Mol Cell. Oct. 1998;2(4):427-36.

Skinner, P.J. et al., Ataxin-1 with an expanded glutamine tract alters nuclear matrix-associated structures. Nature. Oct. 30, 1997;389(6654):971-4. Erratum in: Nature Jan. 15, 1998;391(6664):307.

Smith, D.B. et al., Single-step purification of polypeptides expressed in *Escherichia coli* as fusions with glutathione S-transferase. Gene. Jul. 15, 1988;67(1):31-40.

Tellez-Nagel, I. et al., Studies on brain biopsies of patients with Huntington's chorea. J Neuropathol Exp Neurol. Apr. 1974;33(2):308-32..

Towbin, H. et al., Electrophoretic transfer of proteins from polyacrylamide gels to nitrocellulose sheets: procedure and some applications. Proc Natl Acad Sci U S A. Sep. 1979;76(9):4350-4.

Trottier, Y. et al., Cellular localization of the Huntington's disease protein and discrimination of the normal and mutated form. Nat Genet. May 1995;10(1):104-10.

Vonsattel, J.-P. et al., Neuropathological classification of Huntington's disease. J Neuropathol Exp Neurol. Nov. 1985;44(6):559-77.

Wanker, E.E. et al., HIP-I: a huntingtin interacting protein isolated by the yeast two-hybrid system. Hum Mol Genet. Mar. 1997;6(3):487-95.

Millipore Webpage, Immobilon™ Transfer Membranes: for superior protein and nucleic acid blots.

Millipore Webpage, Immobilon™ -P Transfer Membrane, Introduction.

Athanasou, N.A. Dialysis Amyloid, Chapter 8: Description, localization, and progression of β2-microglobulin dialysis-related amyloid deposition. 1996; 173-191.

Kelly, J.W. Alternative conformations of amyloidogenic proteins govern their behavior. Curr Opin Struct Biol. Feb. 1996;6(1):11-7.

Perler, F.B. et al., Compilation and analysis of intein sequences. Nucleic Acids Res. Mar. 15, 1997;25(6):1087-93.

Wanker, E.E. and Droge, A. Huntington's Disease, $3^{rd}$ Edition, Chapter 11: Structural Biology of Huntington's Disease 2002;327-340.

Spillantini et al., Comparison of the neurofibrillary pathology in Alzheimer's disease and familial presenile dementia with tangles. Acta Neuropathol. 1996, 92:42-48.

* cited by examiner

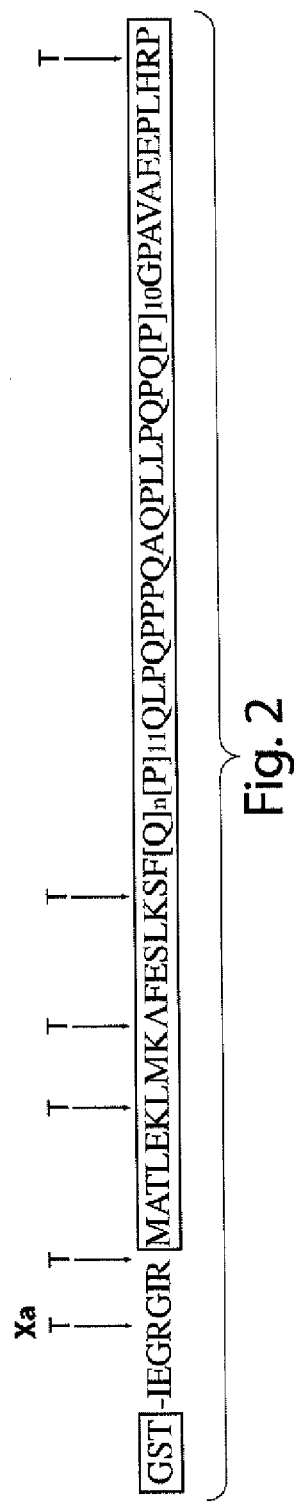
Fig. 2
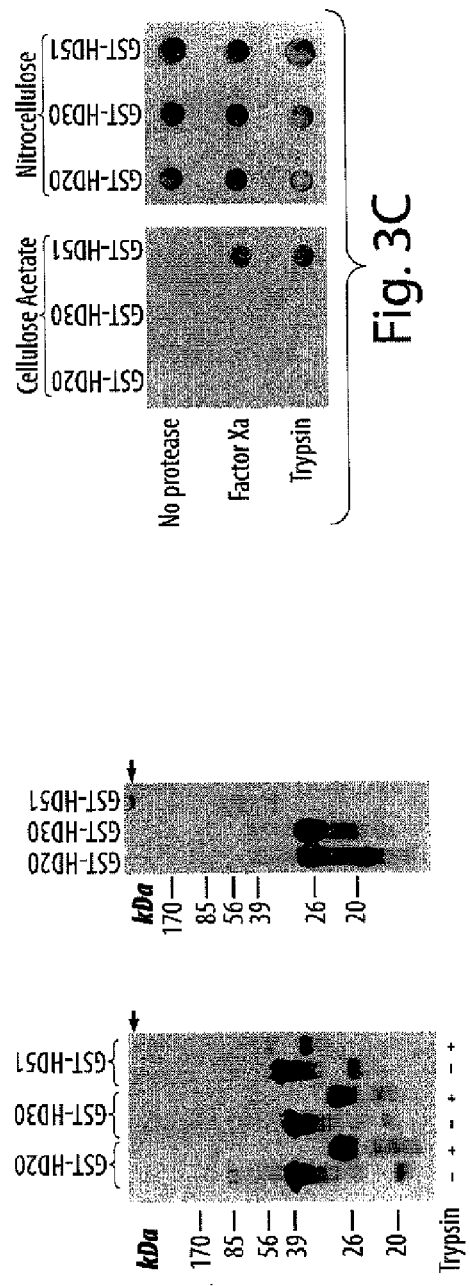
Fig. 3A
Fig. 3B
Fig. 3C

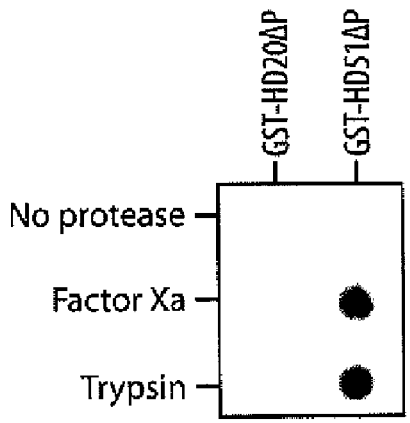
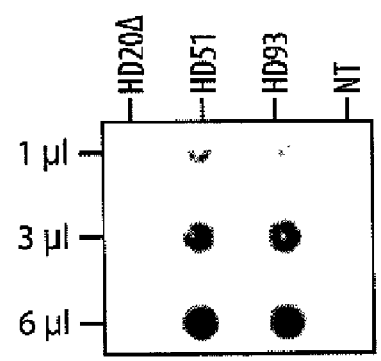
Fig. 9A  Fig. 9C
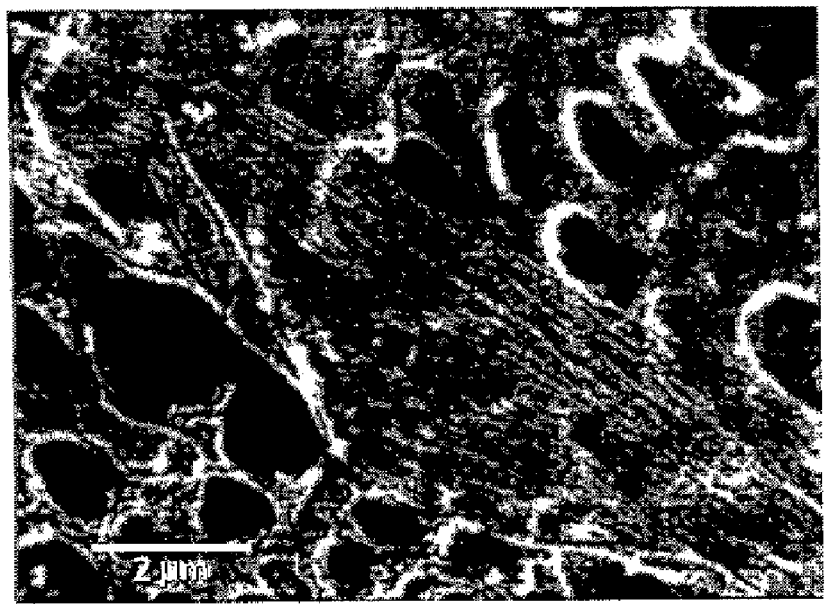
Fig. 9B

SEQUENCE LISTING

```
<160> NUMBER OF SEQ ID NOS: 10

<210> SEQ ID NO 1
<211> LENGTH: 38
<212> TYPE: DNA
<213> ORGANISM: Artificial Sequence
<220> FEATURE:
<223> OTHER INFORMATION: Oligonucleotide Primer

<400> SEQUENCE: 1
tgggatccgc atggcgaccc tggaaaagct gatgaagg                        38

<210> SEQ ID NO 2
<211> LENGTH: 36
<212> TYPE: DNA
<213> ORGANISM: Artificial Sequence
<220> FEATURE:
<223> OTHER INFORMATION: Oligonucleotide Primer
```

<400> SEQUENCE: 2
ggagtcgact cacggtcggt gcagcggctc ctcagc                                36

<210> SEQ ID NO 3
<211> LENGTH: 39
<212> TYPE: DNA
<213> ORGANISM: Artificial Sequence
<220> FEATURE:
<223> OTHER INFORMATION: Oligonucleotide Sequence

<400> SEQUENCE: 3
ctcctcgagc ggcggtggcg gctgttgctg ctgctgctg                             39

<210> SEQ ID NO 4
<211> LENGTH: 51
<212> TYPE: DNA
<213> ORGANISM: Artificial Sequence
<220> FEATURE:
<223> OTHER INFORMATION: Oligonucleotide Sequence

<400> SEQUENCE: 4
cgctcgaggg tatcttcgag gcccagaaga tcgagtggcg atcaccatga g              51

<210> SEQ ID NO 5
<211> LENGTH: 54
<212> TYPE: DNA
<213> ORGANISM: Artificial Sequence
<220> FEATURE:
<223> OTHER INFORMATION: Oligonucleotide Sequence

<400> SEQUENCE: 5
ggccgctcat ggtgatcgcc actcgatctt ctgggcctcg aagataccct cgag           54

<210> SEQ ID NO 6
<211> LENGTH: 56
<212> TYPE: PRT
<213> ORGANISM: Homo Sapiens

<400> SEQUENCE: 6

Ile Glu Gly Arg Gly Ile Arg Met Ala Thr Leu Glu Lys Leu Met Lys
 1               5                  10                  15

Ala Phe Glu Ser Leu Lys Ser Phe Gln Pro Gln Leu Pro Gln Pro Pro
            20                  25                  30

Pro Gln Ala Gln Pro Leu Leu Pro Gln Pro Gln Pro Gly Pro Ala Val
        35                  40                  45

Ala Glu Glu Pro Leu His Arg Pro
    50                  55

<210> SEQ ID NO 7
<211> LENGTH: 36
<212> TYPE: PRT
<213> ORGANISM: Homo Sapiens

<400> SEQUENCE: 7

Ile Glu Gly Arg Gly Ile Arg Met Ala Thr Leu Glu Lys Leu Met Lys
 1               5                  10                  15

Ala Phe Glu Ser Leu Lys Ser Phe Gln Pro Pro Pro Leu Glu Arg
            20                  25                  30

Pro His Arg Asp
        35

<210> SEQ ID NO 8

```
<211> LENGTH: 36
<212> TYPE: PRT
<213> ORGANISM: Homo Sapiens

<400> SEQUENCE: 8

Ile Glu Gly Arg Gly Ile Arg Met Ala Thr Leu Glu Lys Leu Met Lys
 1               5                   10                  15

Ala Phe Glu Ser Leu Lys Ser Phe Gln Pro Pro Pro Leu Glu Arg
                20                  25                  30

Pro His Arg Asp
        35

<210> SEQ ID NO 9
<211> LENGTH: 44
<212> TYPE: PRT
<213> ORGANISM: Homo Sapiens

<400> SEQUENCE: 9

Ile Glu Gly Arg Gly Ile Arg Met Ala Thr Leu Glu Lys Leu Met Lys
 1               5                   10                  15

Ala Phe Glu Ser Leu Lys Ser Phe Gln Pro Pro Pro Leu Glu Gly
                20                  25                  30

Ile Phe Glu Ala Gln Lys Ile Glu Trp Arg Ser Pro
        35                  40

<210> SEQ ID NO 10
<211> LENGTH: 44
<212> TYPE: PRT
<213> ORGANISM: Homo Sapiens

<400> SEQUENCE: 10

Ile Glu Gly Arg Gly Ile Arg Met Ala Thr Leu Glu Lys Leu Met Lys
 1               5                   10                  15

Ala Phe Glu Ser Leu Lys Ser Phe Gln Pro Pro Pro Leu Glu Gly
                20                  25                  30

Ile Phe Glu Ala Gln Lys Ile Glu Trp Arg Ser Pro
        35                  40
```

METHOD OF DETECTING AMYLOID-LIKE FIBRILS OR PROTEIN AGGREGATES

RELATED APPLICATIONS

This application claims priority to PCT/EP98/04810, filed on Jul. 31, 1998, which claims priority to European Patent Application 97113320.2, filed on Aug. 1, 1997.

FIELD OF THE INVENTION

The present invention relates to methods of detecting the presence of detergentor or urea-insoluble amyloid-like fibrils or protein aggregates on filters. Preferably, said fibrils or aggregates are indicative of a disease, preferably of a neurodegenerative disease such as Alzheimer's disease or Huntington's disease. In addition, the present invention relates to inhibitors identified by the method of the invention, to pharmaceutical compositions comprising said inhibitors and to diagnostic compositions useful for the investigation of said amyloid-like fibrils or aggregates.

BACKGROUND OF THE INVENTION

Amyloid-like fibrils and aggregates are found widespread in nature. For example, protein aggregates are found as inclusion bodies in bacteria. Such inclusion bodies may in particular arise during the recombinant expression of proteins in bacteria. In addition, a variety of diseases, both in humans and animals, is characterized by the pathogenic formation of amyloid-like fibrils or protein aggregates in neuronal tissues. A well-known and typical example of such diseases is Alzheimer's disease (AD). AD is characterized by the formation of neurofibrillar tangles and β-amyloid fibrils in the brain of AD patients. Similarly, scrapie is associated with the occurrence of scrapie-associated fibrils in brain tissue.

Another class of these diseases is characterized by an expansion of CAG repeats in certain genes. The affected proteins display a corresponding polyglutamine expansion. Said diseases are further characterized by a late onset in life and a dominant pathway of inheritance.

A typical representative of this class of diseases is Huntington's disease. Huntington's disease (HD) is an autosomal dominant progressive neurodegenerative disorder characterized by personality changes, motor impairment and subcortical dementia (Harper, 1991). It is associated with a selective neuronal cell death occurring primarily in the cortex and striatum (Vonsattel et al., 1985). The disorder is caused by a CAG/polyglutamine (polygln) repeat expansion in the first exon of a gene encoding a large ~350 kDa protein of unknown function, designated huntingtin (HDCRG, 1993). The CAG repeat is highly polymorphic and varies from 6-39 repeats on chromosomes of unaffected individuals and 35-180 repeats on HD chromosomes (Rubinsztein et al., 1996; Sathasivam et al., 1997). The majority of adult onset cases have expansions ranging from 40-55 units, whereas expansions of 70 and above invariably cause the juvenile form of the disease. The normal and mutant forms of huntingtin have been shown to be expressed at similar levels in the central nervous system and in peripheral tissues (Trottier et al., 1995a). Within the brain, huntingtin was found predominantly in neurons and was present in cell bodies, dentrites and also in the nerve terminals. Immunohistochemistry, electron microscopy and subcellular fractionations have shown that huntingtin is primarily a cytosolic protein associated with vesicles and/or microtubules, suggesting that it plays a functional role in cytoskeletal anchoring or transport of vesicles (DiFiglia et al., 1995; Gutekunst et al., 1995; Sharp et al., 1995) Huntingtin has also been detected in the nucleus (de Rooij et al., 1996; Hoogeveen et al., 1993) suggesting that transcriptional regulation cannot be ruled out as a possible function of this protein.

In addition to HD, CAG/polygin expansions have been found in at least six other inherited neurodegenerative disorders which include: spinal and bulbar muscular atrophy (SBMA), dentatorubral pallidoluysian atrophy (DRPLA), and the spinocerebellar ataxias (SCA) types 1, 2, 3 and 6 (referenced in Bates et al. 1997). The normal and expanded size ranges are comparable with the exception of SCA6 in which the expanded alleles are smaller and the mutation is likely to act by a different route. However, in all cases the CAG repeat is located within the coding region and is translated into a stretch of polygin residues. Although the proteins harboring the polygin sequences are unrelated and mostly of unknown function, it is likely that the mutations act through a similar mechanism. Without exception, these proteins are widely expressed and generally localized in the cytoplasm. However, despite overlapping expression patterns in brain, the neuronal cell death is relatively specific and can differ markedly (Ross, 1995), indicating that additional factors are needed to convey the specific patterns of neurodegeneration.

In the art, there is a variety of methods to determine the presence of amyloid-like fibrils or protein aggregates. For example, inclusion bodies in bacteria can be made visible microscopically. Further, amyloid-like fibrils such as from Alzheimer's disease may be analyzed by complex methodology; see, for example, Booth et al. Nature 385 (1997), 787-793, and references cited therein.

So far, however, a simple method that may be established in any laboratory without sophisticated equipment is not available. Such a method would be especially useful in routine procedures such as the testing of patient samples for amyloid-like fibrils or protein aggregates. Accordingly, the technical problem underlying the present invention was to provide a rather simple method that may routinely be used for the detection of such fibrils or aggregates. The solution to said problem is provided by the embodiment characterized in the claims.

SUMMARY OF THE INVENTION

Thus, the present invention relates to a method of detecting the presence of detergent- or urea-insoluble amyloid-like fibrils or protein aggregates on a filter comprising the steps of (a) contacting said filter with material suspected to comprise said fibrils or aggregates and (b) detecting said fibrils or aggregates are retained on said filter.

In accordance with the present invention, it has surprisingly been found that filters of a variety of consistencies may be employed to retain detergent- or urea-insoluble amyloid-like fibrils or protein aggregates on their surface. Essentially, only the above-recited two steps are necessary in order to investigate whether said fibrils or aggregates are present in a sample.

The first step comprises contacting the filter with material suspected to comprise said fibrils or aggregates. The term "suspected to comprise" is intended to mean that the investigator may start from the assumption that the material indeed contains such fibrils or aggregates. Alternatively, said term means that it is totally unclear whether the material under investigation comprise such fibrils or aggregates.

It may be appropriate to pretreat the material prior to application to the filter. For example, for the detection of inclusion bodies, it may be desirable to first lyse the cells and set the cytoplasmic fraction free. Also, it may be useful to pretreat the patient samples prior to application to the filter. Said pretreatment may be effected, for example by employing proteases.

The detection of fibrils that are retained on the filter (the second step) may also be effected by a variety of steps. For example, detection may be effected by Western blot techniques, if an appropriate antibody is available.

In a preferred embodiment of the method of the invention, said amyloid-like fibrils or protein aggregates are indicative of a disease.

Of particular advantage is the method of the present invention in the detection of amyloid fibrils or protein aggregates that are indicative of human diseases, particularly in routine laboratory methods. This embodiment of the method of the invention allows the rapid determination of the disease state, if any, of the patient. For example, the concentration of amyloid-like fibrils or protein aggregates in tissue may be determined by appropriate dilution series. Using automated systems, the presence of such fibrils or aggregates per se may be determined for a large number of patients on a single filter. A further advantage of the method of the invention is that results are available rather quickly. This has also an impact on the overall cost of the detection method, in particular in routine laboratory diagnosis. Due to the simple set-up of the method of the invention, a large number of routine laboratories, for example in hospitals, can apply the method of the invention without the need to acquire expensive equipment such as electron microscopes.

Thus, particularly preferred is the method where said disease is a human disease.

Further preferred is that said disease is associated with a polyglutamine expansion.

Most preferred is that said disease is Huntington's disease, spinal and bulbar muscular atrophy, dentarorubral pallidoluysian atropy, spinocerebellar ataxia type-1, -2, -3, -6, or -7, Alzheimer's disease, BSE, primary systemic amyloidosis, secondary systemic amyloidosis, senile systemic amyloidosis, familial amyloid polyneuropathy I, hereditary cerebral amyloid angiopathy, hemodialysis-related amyloidosis, familial amyloid polyneuropathy III, Finnish hereditary systemic amyloidosis, type II diabetes, medullary carcinoma of the thyroid, spongiform encephalopathies: Kuru, Gerstmann-Sträussler-Scheinker syndrome (GSS), familial insomnia, scrapie, atrial amyloidosis, hereditary non-neuropathic systemic amyloidosis, injection-localized amyloidosis, hereditary renal amyloidosis, or Parkinson's disease.

In particular, these diseases, for which, as a rule, no simple detection method has been developed so far, can now be assessed by simple laboratory technology.

The filter used in the method of the invention may be any filter with a sufficiently small pore size (0.45 µm and preferably 0.2 µm or smaller). Preferred is that the filter is comprised of material with low protein absorption, and particularly preferred is that the material with low protein absorption of which said filter is comprised is cellulose acetate.

A further preferred embodiment relates to a method wherein, prior to step (b), the following step is carried out:

(b') washing said filter so as to remove detergent- or urea-soluble material. This embodiment is particularly preferred when enhanced sensitivity of detection is required. Such an enhanced sensitivity may be necessary, for example, when the early onset of one of the above-mentioned diseases is assessed because it is envisaged that at an early stage of any of said diseases a rather low amount of fibrils or aggregates may be found in the affected tissue or cells.

Step (b') may be repeated one or several times. The person skilled in the art is in a position to determine appropriate washing conditions without further ado. Preferably, the washing buffer comprises 0.1-2% SDS, 4-8M urea, and 0.1-2% Triton X-100™.

Further preferred is in the method of the invention that the detergent- or urea-soluble material is simultaneously with or subsequent to step (a), sucked through said filter.

This embodiment is particularly useful when a microtitre plate containing a filter membrane or an apparatus for dot-blotting is available. The non-desired detergent- or urea-soluble material may be easily removed applying, for example, such a dot-blot apparatus.

In another preferred embodiment of the invention, detection in step (b) is effected by an antibody, or (poly)peptide, preferably a tag or an enzyme, or a fragment or derivative thereof or a chemical reagent that specifically binds to said fibrils or aggregates.

As regards the antibody, or fragment or derivative thereof, it may be employed in the Western blot type assay to determine the presence of said fibrils or aggregates. Western blot technology is well-known in the art and need not be described here in any more detail.

In another preferred embodiment of the invention, detection in step (b) is effected by electron microscopy, electron scanning microscopy, fluorescence or chemiluminescence.

In a further preferred embodiment of the method of the invention, said material is derived from tissues or cells of bacteria, yeast, fungi, plants, insects, animals, preferably mammals, humans, from a transgenic animal or a transgenic plant.

In accordance with the present invention, it is additionally preferred that the method further comprises the following steps:

(a') incubating a fusion protein comprising a (poly)peptide that enhances solubility and/or prevents aggregation of said fusion protein, an amyloidogenic (poly)peptide that has the ability to self-assemble into amyloid-like fibrils or protein aggregates when released from said fusion protein and a cleavable site that separates the above-mentioned components of the fusion protein in the presence of a suspected inhibitor of amyloid-like fibril or protein aggregate formation; and (a") simultaneously with or after step (a'), further incubating with a compound that induces cleavage at said cleavage site.

This embodiment is particularly advantageous for elucidating the mechanism or basis of amyloid-like fibril or protein aggregate formation. Namely, it has been surprisingly found that proteins of the above composition, after cleavage, aggregate under conditions that are, e.g., described in the appended examples. Thus, fibril or aggregate formation may be monitored under varying conditions and detected by the filter assay of the present invention.

The (poly)peptide that enhances solubility and/or prevents aggregation is preferably glutathione-S-transferase, intein, thioredoxin, dihydroflate reductase, chymotrypsin inhibitor II or a functional fragment or derivative thereof. A functional fragment is a fragment that essentially retains the function of the (poly)peptide. Preferred proteins that have the ability of self-assembling to amyloid-like fibrils or protein aggregates may be selected from the group consisting or huntingtin, androgen receptor, atropin, TATA binding protein, or ataxin-1,-2,-3 or -6 or a fragment or derivative thereof, amyloid precursor protein (APP), β-protein, an immunoglobulin light chain, serum amyloid A, transthyretin, cystatin C, β2-microglobulin, apolipoprotein A-1, gelsoline, islet amyloid polypeptide (IAPP), calcitonin, a prion, atrial natriuretic factor (ANF), lysozyme, insulin, fibrinogen, or α-synuclein.

Incubation conditions may be determined by the person skilled in the art according to conventional procedures. The separation of the two components of the fusion protein also includes that either or both components are degraded to a certain extent. It is, however, important that the capability of the (poly)peptide that has the ability of self-assembling is not lost due to the degradation.

Preferably, the cleavable site is an enzymatically cleavable site or a chemically cleavable site or a site cleavable by intein self-cleavage in the presence of thiols. A number of enzymes that site-specifically or non-site-specifically digest proteinaceous material is known in the art. Examples of such enzymes are factor Xa, thrombin, trypsin, endopeptidases Arg C or Lys C, proteinase K or elastase. Depending on the goal of the experiment, any or most of the known enzymes are applicable to this test. The same holds true for most of the chemical cleavage agents.

In accordance with the present invention, it is most preferred that the method of the invention further comprises, prior to step (b) and after step (a"): (a''') incubation with an inhibitor of said compound that induces cleavage.

This embodiment of the method of the invention allows precise incubation periods of the cleaving agent which may be useful, for example, for studying the kinetics of aggregation.

Figure 7:
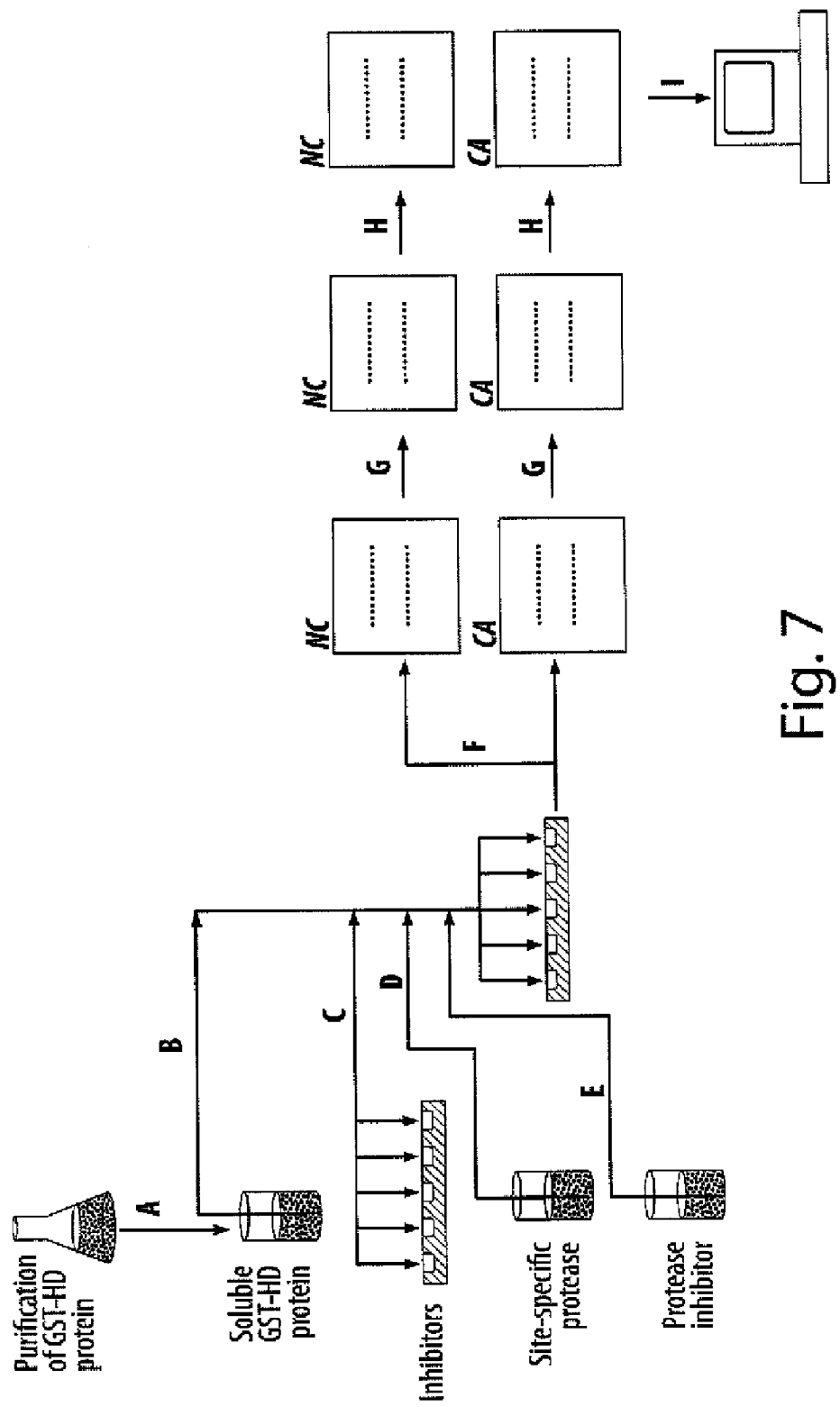

A general overview of the above-recited specific embodiments of the invention relating to the cleaving of fusion protein are detailed in FIG. 7.

It is furthermore particularly preferred that said amyloidogenic (poly)peptide comprises a polyglutamine expansion. As has been demonstrated in the appended examples, the specific embodiments relating to the cleavage of fusion proteins may be advantageously employed for determining fibril or aggregate formation of proteins that comprise polyglutamine expansions. Accordingly, this embodiment is particularly useful for the assessment of the onset or the progress of Huntington's disease, spinal and balba muscular atrophy, dentatorubral pallidoluysian atrophy and the spinocerebral ataxia types 1, 2, 3 and 6.

Further particularly preferred is that the polyglutamine expansion comprises at least 35, preferably at least 41, more preferably at least 48 and most preferably at least 51 glutamines.

The length of the polyglutamine expansions appears to be correlated to the susceptibility of humans or animals to the above-recited diseases. In this regard, we also refer to the European patent application entitled "Novel composition and method for the detection of diseases associated with amyloid-like fibril or protein aggregate formation" filed on the same day with the European Patent Office and assigned to the same applicant. The contents of said application are specifically incorporated herein by reference.

Further preferred is in accordance with the present invention that said contacting is effected by dotting, spotting or pipetting said material onto said filter.

This embodiment is particularly useful for an automated application of the invention. Additionally, the set-up associated with dot-blotting or spot-blotting allows the investigation of a large number of sample materials as well as the cost-conscious application of the method of the invention. This is due to the fact that a large number of samples can be assessed for fibril or aggregate formation on one and the same filter.

It is furthermore preferred that the filter is a filter membrane which is optionally or preferably contained in a microtitre plate. Additionally preferred is the use of SDS as detergent or Triton X-100™ for non-β-amyloid aggregates.

The invention further relates to an inhibitor identified by the method of the invention. While practically any compound class may be tested for inhibitory effects, it is preferred that said inhibitor is an antibody or a derivative or functional fragment thereof, a peptide or a chemical reagent.

Furthermore, the present invention relates to a pharmaceutical composition comprising the inhibitor of the invention and pharmaceutically acceptable carrier and/or diluent. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical or intradermal administration. The dosage regimen will be determined by the attending physician and other clinical factors. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 to 1000 μg (or of nucleic acid for expression or for inhibition of expression in this range); however, doses below or above this exemplary range are envisioned, especially considering the aforementioned factors. Generally, the regimen as a regular administration of the pharmaceutical composition should be in the range of 1 μg to 10 mg units per day. If the regimen is a continuous infusion, it should also be in the range of 1 μg to 10 mg units per kilogram of body weight per minute, respectively. Progress can be monitored by periodic assessment. Dosages will vary but a preferred dosage for intravenous administration of DNA is from approximately $10^6$ to $10^{12}$ copies of the DNA molecule. The compositions of the invention may be administered locally or systemically. Administration will generally be parenterally, e.g., intravenously; DNA may also be administered directly to the target site, e.g., by biolistic delivery to an internal or external target site or by catheter to a site in an artery.

The therapeutically useful compounds identified according to the method of the invention may be administered to a patient by any appropriate method for the particular compound, e.g., orally, intravenously, parenterally, transdermally, transmucosally, or by surgery or implantation (e.g., with the compound being in the form of a solid or semi-solid biologically compatible and resorbable matrix) at or near the site where the effect of the compound is desired.

The invention further relates to diagnostic composition comprising (i) a fusion protein as defined in the invention.

Preferably, the diagnostic composition further comprises (ii) a filter as defined in the invention optionally or preferably combined in a microtitre plate; and optionally (iii) a compound that induces cleavage as defined in any one of the preceding claims; and optionally (iv) an inhibitor of said compound of (c); and optionally (v) suitable buffer solutions.

The diagnostic composition of the invention may be used for a variety of purposes. For example, it may be used for detecting the presence, etiology or status of one of the above-mentioned diseases or a corresponding disease state in a patient. In addition, it may be used for the development of suitable inhibitors of the formation of amyloid-like fibrils or protein aggregates that are preferably, but not exclusively, associated with the above-recited disease states.

The components of the composition of the invention may be packaged in containers such as vials, optionally in buffers and/or solutions. If appropriate, one or more of said components may be packaged in one and the same container.

DESCRIPTION OF FIGURES, SEQUENCES AND EMBODIMENTS

FIG. 1

SDS-PAGE Analysis of Purified GST and GST-HD Fusion Proteins.

(a) Aliquots (15 ml) of eluates from the gluatathione agarose column were subjected to 12.5% SDS-PAGE and analyzed by staining with Coomassie blue R. Lanes 1-6 contain GST, GST-HD20, -HD30, -HD83 and -HD122, respectively.

FIG. 2

Structure of GST-HD Fusion Proteins.

The amino acid sequence corresponding to exon 1 of huntingtin is boxed. Arrows labeled Xa and T indicate cleavage sites for factor Xa and trypsin, respectively.

FIG. 3

Site-Specific Proteolysis of GST-HD Fusion Proteins with Trypsin and Factor Xa.

Tryptic digestions were performed at 37° C. for 3 (a) or 16 h (b). Native proteins and their cleavage products were subjected to 12.5% SDS-PAGE, blotted onto nitrocellulose membranes, and probed with anti-HD1 antibody. Arrows mark the origin of electrophoresis. (c) Purified fusion proteins and their factor Xa and trypsin cleavage products were analyzed using the filter retardation assay. The proteins retained by the cellulose acetate and nitrocellulose membranes were detected by incubation with the anti-HD1 antibody.

FIG. 4

Electron Micrographs of Native GST-HD Fusion Proteins and their Factor Xa and Trypsin Cleavage Products.

Purified GST fusion proteins were protease treated, negatively stained with uranyl acetate and viewed by electron microscopy. The undigested GST-HD51 molecules appear as a homogeneous population of small, round particles (a).

Removal of the GST-tag with factor Xa results in the formation of amyloid-like fibrils and intermediate structures (b+c). After partial digestion (3 h) of GST-HD51 with trypsin, the ribbons are associated with terminal clots (d, arrow), whereas prolonged digestion (16 h) produces ribbons without attached clots (e). Removal of the GST-tag from GST-HD20 shows no evidence for the formation of defined structures (f).

FIG. 5

Birefringence of Protein Aggregates Formed by Proteolytic Cleavage of GST-HD51.

The protein aggregates were stained with Congo red. (a) Bright field, 200×; (b) Polarized light, 200×; (c) Polarized light, 100×.

FIG. 6

Polygin-Containing Protein Aggregates are Formed In Vivo.

(a) Western blot analysis, after separation by 10% SDS-PAGE, of the nuclear (N) and cytosolic (C) protein fractions prepared from brain and kidney of an R6/2 hemizygous transgenic mouse and a littermate control. Blots were probed with anti-HD1, anti-GAPDH and anti-Fos B antibodies as indicated. (b) Detection of HD exon 1 protein aggregates formed in vivo using the cellulose acetate filter assay. The membrane was immunostained using the anti-HD1 antibody. (c) Ultrastructure of a neuronal intranuclear inclusion (NII). The presence of a NII in a striatal neuron of a 17 month old R6/5 homozygous mouse is shown. The NII is indicated by the large arrow and the fibrillar amyloid-like structures within the NII are indicated by two small arrows. The scale bar is 250 nm.

FIG. 7

A: Purification of GST-HD fusion proteins containing polyglutamine expansions by affinity chromatography B: Transfer of soluble GST-HD fusion protein into a microtiter plate using a pipetting robot C: Transfer of various inhibitors into the microtiter plate using a pipetting robot D: Transfer of a protease to the microtiter plate using a pipetting robot to start the formation of insoluble protein fibrils. Incubation of the microtiter plate at 25° C.-37° C. to allow fibril formation E: Addition of a protease inhibitor to stop the cleavage reaction using a pipetting robot F: Transfer of the reaction mixtures onto a cellulose acetate (CA) and a nitrocellulose membrane (NC) using a spotting robot or a pipetting robot G: Washing of the CA membrane with SDS-buffer to remove soluble proteins and the NC membrane with blocking buffer H: Detection of the proteins bound to the CA and NC membranes by Western blot analysis using a specific antibody I: Comparison of the membranes and identification of compounds that block fibril formation using specific computer programs

FIG. 8

Structure of GST-HD fusion proteins. The amino acids sequence corresponding to the N-terminal portion of huntingtin is boxed and the amino acids corresponding to the biotinylation site are underlined. Arrows labeled (Xa) and (T) indicate cleavage sites for factor Xa and trypsin, respectively.

FIG. 9

Detection of polyglutamine-containing protein aggregates formed in vitro and in transfected COS-1 cells using the dot-blot filter retardation assay. (A) Purified GST-HD20DP and -HD51DP fusion proteins (250 ng) and their factor Xa and trypsin cleavage products were applied to the filter as indicated. The aggregated proteins retained by the cellulose acetate membrane were detected by incubation with the anti-HD1 antibody. (B) Scanning electron micrograph of aggregated GST-HD51DP trypsin cleavage products retained on the surface of the cellulose acetate membrane (Photo: Heinrich Lündsdorf, GBF Braunschweig, Germany). (C) Dot-blot filter retardation assay performed on the insoluble fraction isolated from transfected and non-transfected COS-1 cells. COS-1 cells were transiently transfected with the plasmids pTL1-CAG20, -CAG51 and CAG93 encoding huntingtin exon 1 proteins with 20 (HD20), 51 (HD51) and 93 (HD93) glutamines, respectively. The pellet fractions obtained after centrifugation of whole cell lysates were subjected to DNase1/trypsin digestion, boiled in 2% SDS, and portions of 1, 3 and 6 μl were filtered through a cellulose acetate membrane. The aggregated huntingtin protein retained on the membrane was detected with the anti-HD1 antibody. NT, non-transfected cells.

FIG. 10

Detection and quantification of aggregates formed in vitro from biotinylated GST-HD exon 1 fusion proteins. Various amounts of the fusion proteins GST-HD51 DPBio and -HD20DPBio were filtered through a cellulose acetate membrane after a 3-h incubation at 37° C. in the presence or absence of trypsin as indicated. (A) Images of the retained protein aggregates, detected with streptavidin-AP conjugate using either a fluorescent (upper panel) or a chemiluminescent AP substrate (lower panel). (B) Quantification of signal intensities obtained for the GST-HD51DPBio dots seen in A. Fluorescence and chemiluminescence values are arbitrary units generated by the Lumi-Imager F1 and LumiAnalyst™ software (Boehringer Mannheim).

FIG. 11

Detection (A) and quantification (B) of aggregates formed in vitro from biotinylated GST-HD exon 1 fusion proteins using the dot-blot and microtitre plate filter retardation assay. Various amounts of the fusion proteins GST-HD51DPBio and -HD20DPBio were filtered through the cellulose acetate membranes after a 3-h incubation at 37° C. in the presence or absence of trypsin as indicated. The detection and quantification of the aggregates was as described in FIG. 3.

FIG. 12

Detection of neurofibrillar tangles (NFTs) and β-amyloids in brain extracts prepared from Alzheimer's disease patients and controls using the dot-blot filter retardation assay. The cellulose acetate membrane was probed with the polyclonal anti-Tau, the Monoclonal anti-β-amyloid, or the polyclonal anti-HD antibody, A1, A2, and A3: protein extracts prepared from cerebral cortex of Alzheimer's disease patients; C1, C2, and C3: protein extracts prepared from cerebral cortex of normal individuals. GST-HD51, fusion of glutathione S-transferase and huntingtin exon 1 containing 51 glutamines.

SEQUENCES

SEQ ID NO: 1 is a primer (ES25) having the following sequence: TGGGATCCGC ATGGCGACCC TGGAAAAGCT GATGAAGG SEQ ID NO: 2 is a primer (ES26) having the following sequence: GGAGTCGACT CACGGTCGGT GCAGCGGCTC CTCAGC SEQ ID NO: 3 is a primer (ES27) having the following sequence: CTCCTCGAGC GGCGGTGGCG GCTGTTGCTG CTGCTGCTG SEQ ID NO: 4 is a primer (BIO1) having the following sequence: CGCTCGAGGG TATCTTCGAG GCCCAGAAGA TCGAGTGGCG ATCACCATGA G SEQ ID NO: 5 is a primer (BIO2) having the following sequence: GGCCGCTCAT GGTGATCGCC ACTCGATCTT CTGGGCCTCG AAGATACCCT CGAG SEQ ID NO: 6 is a peptide having the following sequence:

Ile Glu Gly Arg Gly Ile Arg Met Ala Thr Leu Glu Lys Leu Met Lys Ala Phe Glu Ser Leu Lys Ser Phe (Gln)$_n$ (Pro)$_{11}$ Gln Leu Pro Gln Pro Pro Pro Gln Ala Gln Pro Leu Leu Pro Gln Pro Gln (Pro)$_{10}$ Gly Pro Ala Val Ala Glu Glu Pro Leu His Arg Pro

SEQ ID NO: 7 is a peptide having the following sequence:

Ile Glu Gly Arg Gly Ile Arg Met Ala Thr Leu Giu Lys Leu Met Lys Ala Phe Glu Ser Leu Lys Ser Phe (Gln)$_{20}$ Pro Pro Pro Pro Leu Glu Arg Pro His Arg Asp

SEQ ID NO: 8 is a peptide having the following sequence:

Ile Glu Gly Arg Gly Ile Arg Met Ala Thr Leu Glu Lys Leu Met Lys Ala Phe Glu Ser Leu Lys Ser Phe (Gln)$_{51}$ Pro Pro Pro Pro Leu Glu Arg Pro His Arg Asp

SEQ ID NO: 9 is a peptide having the following sequence:

Ile Glu Gly Arg Gly Ile Arg Met Ala Thr Leu Glu Lys Leu Met Lys Ala Phe Glu Ser Leu Lys Ser Phe Gln$_{20}$ Pro Pro Pro Pro Leu Glu Gly Ile Phe Glu Ala Gln Lys Ile Glu Trp Arg Ser Pro

SEQ ID NO: 10 is a peptide having the following sequence:

Ile Glu Gly Arg Gly Ile Arg Met Ala Thr Leu Gln Lys Leu Met Lys Ala Phe Glu Ser Leu Lys Ser Phe (Gln)$_{51}$ Pro Pro Pro Pro Leu Gln Gly Ile Phe Glu Ala Gln Lys Ile Glu Trp Arg Ser Pro

The examples illustrate the invention:

EXAMPLE 1

Purification of GST-HD Fusion Proteins Containing Expanded Polyglns

Figure 1B:
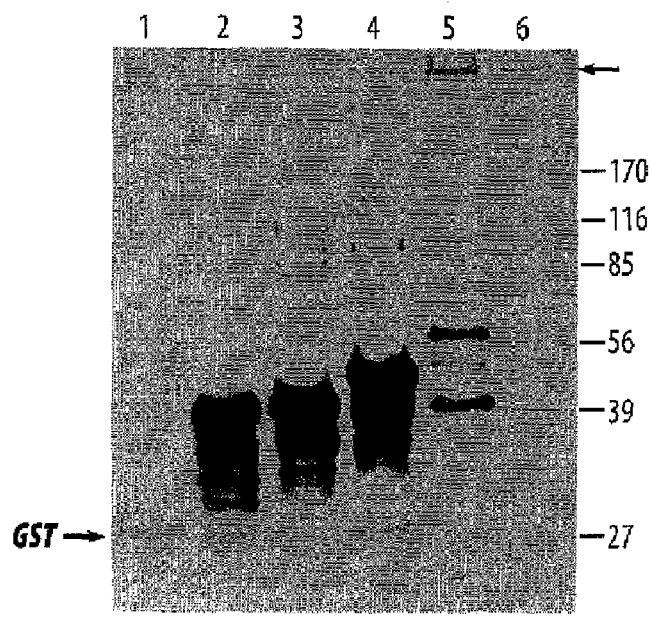

Exon 1 of the HD gene was isolated from genomic phage clones, derived from the normal and expanded alleles of an HD patient (Sathasivam et al., 1997), and used for the expression of GST-HD fusion proteins in *E. coli*. DNA fragments containing CAG repeats in the normal (CAG)$_{20-33}$ and expanded (CAG)$_{37-130}$ range were cloned into pGEX-5X-1 (Pharmacia), and the resulting plasmids expressing fusion proteins with 20 (GST-HD20), 30 (-HD30), 51 (-HD51), 83 (-HD83) and 122 (-HD122) glutamines, respectively, were used for protein purification. For plasmid construction lambda phage from stock 9197$_4$ (Sathasivam et al., 1997) were plated single plaques which were innoculated into 400 ml cultures of *E. coli* XL1-Blue MRF' (Stratagene) for DNA preparation. The DNA sequence encoding the N-terminal portion of huntingtin (exon 1), including the CAG repeats, was amplified by PCR using the following pair of primers: ES 25 (TG GGATCCGCATGGCGACCCTGGAAAAGCTGATGAA GG) (Seq. ID No. 1) corresponding to nt315-343 of the HD gene (HDCRG, 1993) and containing a BamHI site (underlined) and ES 26 (GGAGTCGACTCACGGTCGGTGCAGC GCTCCTCAGC) (Seq. ID No. 2) corresponding to nt516-588 and containing a SalI site (underlined). Conditions for PCR were as described (Mangiarini et al. 1996). Due to instability of the CAG repeat during propagation in *E. coli*, DNA preparations from individual plaques yielded different sized PCR products. Fragments of ~320, 360, 480, and 590 bp were gel-purified, digested with BamHI and SalI and inserted into the BamHI-SalI site of the expression vector pGEX-5X1 (Pharmacia) yielding pCAG30, pCAG51, pCAG83 and pCAG122, respectively. PCAG20, containing 20 repeats of CAG within the cloned HD exon 1 sequence, was similarly constructed from a phage genomic clone derived from a normal allele. All constructs were verified by sequencing. After induction with IPTG, the resulting proteins were purified under native conditions by affinity chromatography on glutathione agarose. Thus, *E. coli* SCSI (Stratagene) carrying the pGEX expression plasmid of interest was grown to an OD$_{600nm}$ of 0.6 and induced with IPTG (1 mM0 for 3.5 h as described in the manufacturer's protocol (Pharmacia). Cultures (200 ml) of induced bacteria were centrifuged at 4000 g for 20 min, and the resulting pellets were stored at −80° C. Cells were thawed on ice and resuspended in 5 ml of lysis buffer (50 mM sodium phosphate, 150 mM NaCl, 1 mM EDTA, pH 7.4) containing 0.5 mg/ml lysozyme. After 45 min at 0° C., cells were sonicated with two 30 sec-bursts. Octyl-β-D-glucopyranoside was then added to a final concentration of 0.1% and the resulting lysate was clarified by centrifugation at 30,000 g for 30 min at 4° C. Cleared lysates were incubated for 1 h at 4° C. with 500 μl of a 1:1 slurry of glutathione-agarose beads (Sigma) that had been washed times and resuspended in lysis buffer. The beads were poured into a small column and washed extensively with lysis buffer containing 0.1% octyl-β-D-glucopyranoside. The bound fusion protein was eluted with 2 ml of 15 mM glutathione (reduced) in lysis buffer. Typical yields were 0.5-1 mg of purified GST-HD20, -HD30 and —HD51 proteins per 200 ml of bacterial culture; yields of GST-HD83 and -HD122 were much lower, less than 10% of that obtained with the shorter fusion proteins. Protein was determined by the Bio-Rad dye binding assay using bovine serum albumin as standard. SDS-PAGE of the purified GST-HD20, -HD30, -HD51, -HD83 and -HD122 proteins revealed major bands of 42, 45, 50, 65 and 75 kDa, respectively (FIG. 1a). These bands were also detected when the various protein fractions were subjected to immunoblot analysis using the affinity purified anti-huntingtin antibody HD1 (FIG. 1b, lanes 2-6). HD1 specifically detects the GST-HD fusion proteins on immunoblots, whereas the GST-tag alone is not recognized (FIG. 1b, lane 1). For immunoblotting a bacterial plasmid encoding HD1-His, a His 6-tagged fusion protein containing residues 1-222 of huntingtin, was generated by inserting a PCR-amplified IT-15 cDNA fragment into the pQE-32 vector (Qiagen). The fusion protein was expressed in E. coli, affinity-purified under denaturating conditions on Ni-NTA agarose, and injected into rabbits. The resulting immune serum was then affinity-purified against the antigen that had been immobilized on Ni-NTA agarose. The GAPDH- and Fos B-specific antisera have been described (Wanker et al., 1997; Davies et al., 1997).

Western blotting was performed as detailed (Towbin et al., 1979). The blots were incubated with 1:1000 dilutions of the indicated primary antibody, followed by an alkaline-phosphatase-conjugated secondary antibody. Color development was carried out with 5-bromo-4-chloro-3-indolyl phosphate and nitroblue, tetrazolium as substrates (Promega).

All recombinant proteins migrated at a size corresponding nearly to that predicted from their amino acid sequence. Interestingly, an additional high molecular weight band which remains at the top of the gel, was consistently detected in the protein fractions with the longest polyglns (83 and 122 residues; FIGS. 1a and b, lane 5 and 6). This band was most prominent on the immunoblots but was also clearly detectable in the Commassie stained gel. This immunoreactive material was often still present at the bottom of the loading slots, even after the samples had been boiled for 5 min in the presence of 2% SDS and 6 M urea prior to loading.

EXAMPLE 2

Proteolytic Cleavage of GST-HD Fusion Proteins Containing Expanded Polyglns

It has been shown previously that the solubility of certain proteins can be enhanced by the addition of the GST-tag (Smith and Johnson, 1988) and it was therefore of interest to determine whether the removal of the GST-tag by proteolytic cleavage would have an effect on the solubility of the polygln-containing fusion proteins. Potential factor Xa and trypsin cleavage sites within the GST-HD fusion proteins are shown in FIG. 2. Factor Xa cleaves between the GST-tag and the HD exon 1 protein whereas trypsin removes an additional 15 amino acids from the N-terminus and a single proline from the C-terminus, both proteases leaving the polygln repeat intact. The GST-HD20, -HD30 and -HD51 proteins were digested with trypsin under conditions designed to remove the GST-tag from the fusion protein without it being totally degraded. After cleavage, proteins were denatured by boiling in the presence of 2% SDS and analyzed by SDS-PAGE and immunoblotting using the anti-HD1 antibody. GST-HD20 and -HD30 cleavage yielded products migrating in a 12.5% gel at approximately 30 and 33 kDa, respectively. In contrast, cleavage of GST-HD51 resulted in the formation of two protein products migrating at approximately 37 and 60 kDa, and an additional weak immunoreactive band on the bottom of the loading slots was also detected (FIG. 3a). This high molecular weight band was more pronounced when GST-HD51 was digested with trypsin under conditions in which the GST-tag was totally degraded (FIG. 3b). However, with proteins GST-HD20 and -HD30 this longer exposure to trypsin produced the same cleavage products as the ones seen in FIG. 3a and the high molecular weight products were not observed. Similar results were obtained with factor Xa protease and endoproteinases Arg-C and Lys-C. As regards the proteolytic cleavages, the following protocols were carried out: The GST-HD fusion proteins purified as described above were dialysed against 40 mM Tris-HCl (pH 8.0), 150 mM NaCl, 0.1 mM EDTA and 5% (v/v) glycerol to raise the pH prior to proteolytic cleavage. The proteins were then combined with bovine factor Xa (New England Biolabs) or modified trypsin (Boehringer Mannheim, sequencing grade) in dialysis buffer containing 2 mM $CaCl_2$ at an enzyme:substrate ratio of 1:10 (w/w) or 1:40 (w/w), respectively. Incubations with factor Xa were at. 25° C. for 16 h. Tryptic digestions were performed at 37° C. for 3 or 16 h as indicated. Digestions were terminated by the addition of PMSF to 1 mM . The degree of proteolysis was determined by SDS-PAGE followed by staining with Coomassie blue or immunoblotting using anti-HD1 antibody.

We have developed a simple and sensitive filter assay to detect the formation of high molecular weight insoluble protein aggregates. This assay is based on the finding that the SDS-insoluble protein aggregates obtained by proteolytic cleavage of GST-HD51 are retained on a cellulose acetate filter, whereas the soluble cleavage products of GST-HD20 and -HD30 are not. Factor Xa or trypsin digestions of purified GST-HD fusion proteins (10 μg) were performed in a 20 μl reaction mixture as described above. Reactions were terminated by adjusting the mixture to 2% SDS and 50 mM DTT. After heating at 100° C. for 5 min, aliqouts (0.5 μl) were diluted into 200 μl of 0.1% SDS and filtered through a cellulose acetate membrane (Schleicher & Schuell, 0.2 μm pore size) using a BRL dot blot filtration unit. Filters were washed with water, and the SDS-insoluble aggregates retained on the filter detected by incubation with the anti-HD1 antibody, followed by an anti-rabbit secondary antibody conjugated to alkaline phosphatase (Boehringer Mannheim). FIG. 3c shows immunoblots of cellulose acetate and nitrocellulose membranes to which the native GST-HD20, -HD30 and -HD51 proteins and their factor Xa and trypsin cleavage products have been applied. On the cellulose acetate filter, only the cleavage products of GST-HD51 were detected by the anti-HD1 antibody, indicating the formation of insoluble high molecular weight protein aggregates. In contrast, all the uncleaved GST-HD fusion proteins and their digestion products were detected on the nitrocellulose control filter. This assay was also used to detect huntingtin aggregates present in a nuclear fraction from the brain of an R6/2 hemizygous mouse and littermate control (see preparation of nuclei below).

EXAMPLE 3

Figure 4A:
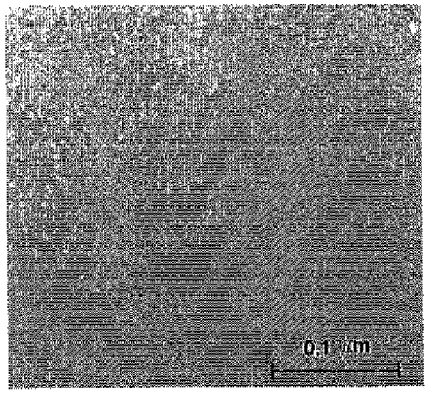
Figure 4B:
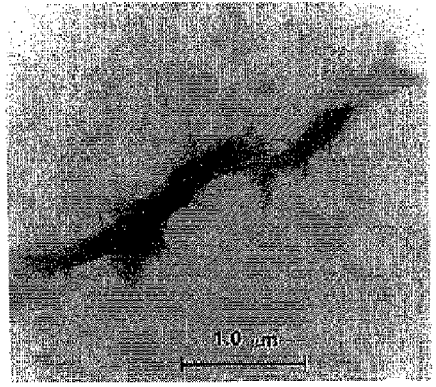
Figure 4C:
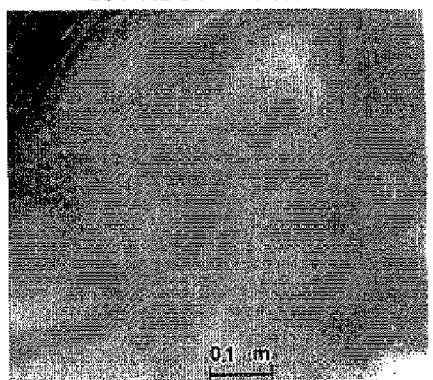
Figure 4D:
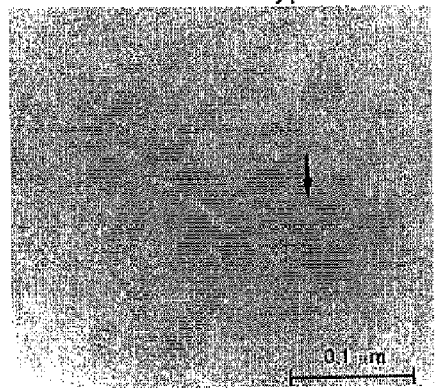
Figure 4E:
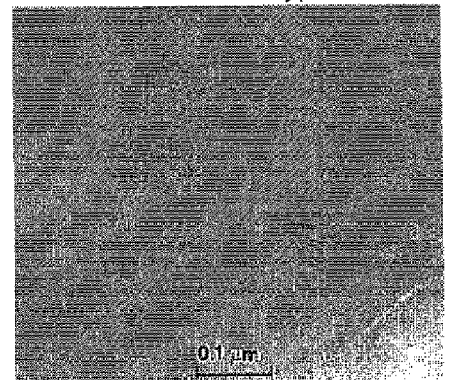
Figure 4F:
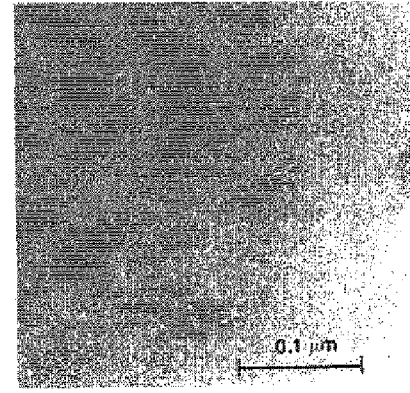

Huntingtin Proteins Containing Expanded Polyglns in the Pathological Range Aggregate to Amyloid-Like Birefringent Fibrils Electron microscopy of negatively stained GST-HD51 fractions showed oligomeric particles with diameters of 6 to 7 nm (FIG. 4a); no higher ordered aggregates were observed. For electron microscopic observation, the native or protease-digested GST-HD fusion proteins were adjusted to a final concentration of 50 μg/ml in 40 mM Tris-HCl (pH 8.0), 150 mM NaCl, 0.1 mM EDTA and 5% glycerol. Samples were negatively stained with 1% uranyl acetate and viewed in a Philips CM100 EM. In contrast, protein fractions obtained by proteolytic cleavage of GST-HD51 showed numerous clusters of high molecular weight fibrils and ribbon-like structures (FIGS. 4b, c, d and e), reminiscent of purified amyloids (Prusiner et al., 1983). The fibrils obtained after digestion with factor Xa showed a diameter of 10-12 nm and their length varied from 100 nm up to several micrometers (FIGS. 4b and c). In the trypsin-treated samples ribbon-like structures formed by lateral aggregation of fibrils with a diameter of 7.7 nm were observed (FIGS. 4d and e). After treatment with factor Xa or limited digestion with trypsin, clots of small particles were frequently detected on one or both ends of the fibrils (FIGS. 4b, c and d). These clots of varying sizes and shapes were not seen when GST-HD51 was digested with trypsin under conditions in which the GST-tag is totally degraded (FIG. 4e), indicating that they contain GST. In strong contrast to GST-HD51, the GST-HD20 and -HD30 proteins did not show any tendency to form ordered high molecular weight structures, either with or without protease treatment (FIG. 4f).

Figure 5A:
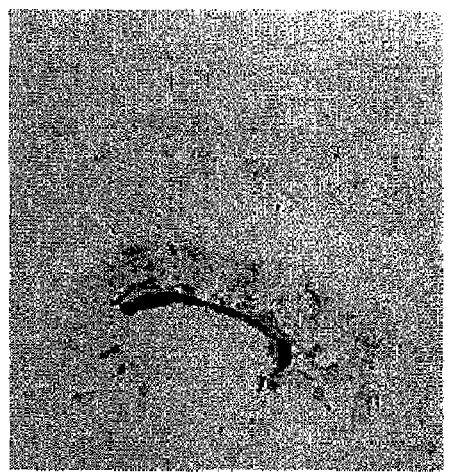
Figure 5B:
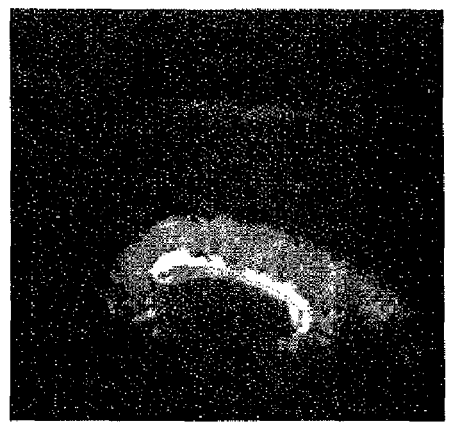
Figure 5C:

The insoluble protein aggregates formed by proteolytic cleavage of GST-HD51 were isolated by centrifugation and stained with Congo red (Caputo et al., 1992) and examined under a light microscope. For light microscopy, peptide aggregates formed by trypsin digestion of purified GST-HD fusion proteins (50 μg in 100 μl of digestion buffer) were collected by centrifugation at 30,000 g for 1 h and resuspended in 10 μl of water. Samples were mixed with 0.1 volume of a 2% (w/v) aqueous Congo Red (Sigma) solution, placed on aminoalkylsilane-coated glass slides, and allowed to dry overnight under a coverslip. After removing the coverslip, excess Congo Red was removed by washing with 90% ethanol. Evaluation of the Congo Red staining by polarization microscopy was performed using a Zeiss Axiolab Pol microscope equipped with strain-free lenses and optimally aligned cross-polarizers. After staining, the protein aggregates on the glass slides were red, indicating that they had bound the dye (FIG. 5a), and when examined under polarized light a green color and birefringence were detected (FIGS. 5b and c). These staining characteristics were similar to those observed for prions (Prusiner et al., 1983) and amyloids (Caputo et al., 1992).

EXAMPLE 4

Figure 6A:
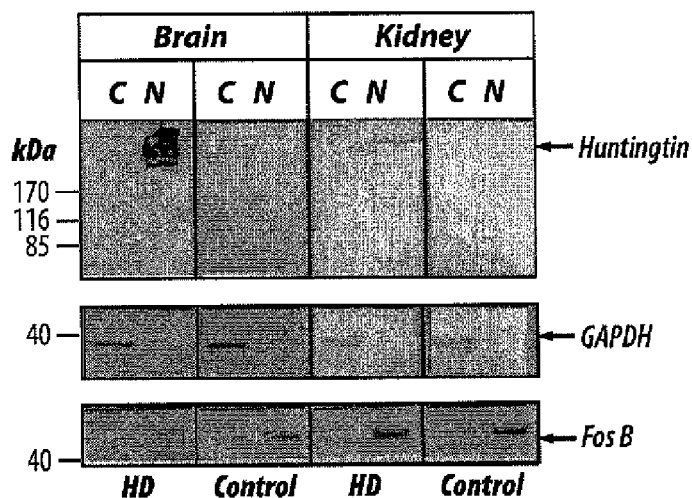
Figure 6B:
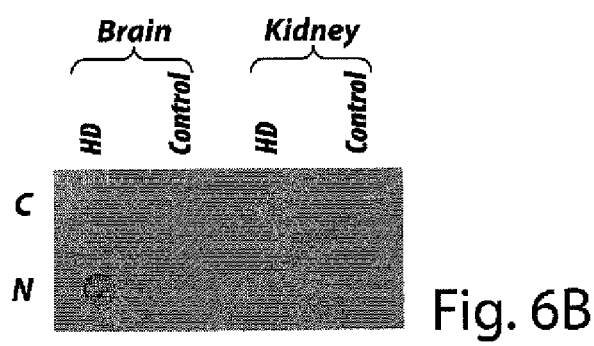

Huntingtin Proteins Containing Expanded PolyGlns Form Amyloid-Like Protein Aggregates In Vivo To determine whether the amyloid-like protein aggregates formed by proteolytic cleavage of GST-HD51 in vitro are also present in vivo, nuclear protein fractions of brain and kidney were prepared from mice transgenic for the HD mutation (line R6/2) and littermate controls (Davies et al., 1997; Mangiarini et al., 1996). Nuclei from the brain or kidney of an R6/2 hemizygous mouse with a repeat expansion of $(CAG)_{143}$ (Mangiarini et al., 1996) at ten weeks of age and littermate control were prepared as follows. Whole brain samples (80 mg) in 400 ml of 0.25 M sucrose in buffer A (50 mM triethanolamine [pH 7.5], 25 mM KCl, 5 mM $MgCl_2$, 0.5 mM DTT, 0.5 mM PMSF) were homogenized using 15 strokes of a tight-fitting glass homogenizer. The homogenate was adjusted to a final concentration of 5 mM DTT, and centrifuged at 800 g for 15 min. The supernatant was recentrifuged at 100,000 g for 1 h, and the supernatant from this centrifugation was taken as the cytosolic fraction (fraction C). The loose pellet from the first centrifugation was homogenized, diluted to 1.2 ml with 0.25 M sucrose/buffer A, and mixed with two volumes of 2.3 M sucrose/buffer A. The mixture was then layered on top of 0.6 ml 2.3 M sucrose/bufferA in a SW60 tube and centrifuged at 124,000 g for 1 h. The pellet was harvested with a spatula, resuspended in 200 μl of 0.25 M sucrose/buffer A and again centrifuged at 800 g for 15 min. The entire procedure was carried out at 4° C. The pelleted nuclei were resuspended to a density of ~1×10$^7$ nuclei/ml in 0.25 sucrose/buffer A (fraction N) and stored at −80° C. Nuclei from mouse kidney were prepared in the same way. The protein extracts were analyzed by SDS-PAGE and Western blotting using the anti-HD1 antibody (FIG. 6a). Strikingly, this antibody detected a prominent high molecular weight band in the nuclear fraction (N) prepared from R6/2 transgenic brain, very similar to the high molecular weight band obtained by proteolytic cleavage of GST-HD51 (FIG. 3b). No such immunoreactive band was detected in the nuclear fraction of brain from the littermate control and it was also absent from the corresponding cytoplasmic fractions (C). A small amount of high molecular weight material was also detected in the nuclear fraction prepared from R6/2 transgenic kidney, but was again absent from the cytoplasmic fraction. The purity of the nuclear and cytoplasmic fractions was confirmed by Western blot analysis using the anti-Fos B and anti-GAPDH antibodies. Anti-Fos B detected the transcription factor mainly in the nuclear fraction, and the enzyme GAPDH was only seen in the cytoplasmic fraction, as expected. The Western blot results were reproduced using the cellulose acetate filter assay (FIG. 6b). Using this assay, a 10-20 fold higher amount of transgene protein was detected in the nuclear fraction isolated from brain material, compared to that prepared from kidney.

The formation of NIIs has been shown to preceed the neuronal dysfunction that forms the basis of the progressive neurological phenotype observed in the R6 transgenic lines (Davies et al., 1997). These NIIs are immunoreactive for both huntingtin and ubiquitin antibodies and contain the transgene but not the endogenous huntingtin protein. Therefore, Western blot analysis using an anti-ubiquitin antibody was also performed showing the same pattern of immunoreactivity as had been observed with the anti-HD1 antibody (FIG. 6a), and indicating that the high molecular weight transgene protein present in the nuclear fraction is ubiquitinated (data not shown).

Figure 6C:
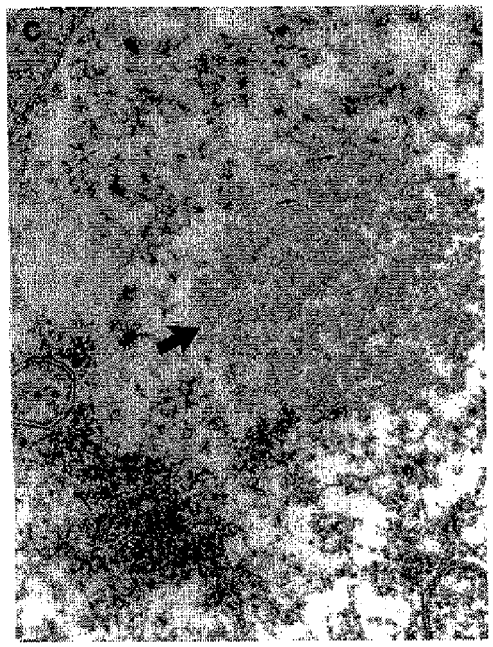

To examine whether the NIIs containing the proteins huntingtin and ubiquitin (Davies et al., 1997) have a fibrous composition, an ultrastructural analysis was performed. Experimentally, a 17 month old R6/5 homozygous mouse $((CAG)_{128-155})$ (Mangiarini et al., 1996) was deeply anaesthetized with sodium pentobarbitone and then perfused through the left cardiac ventricle with 35-50 ml of 4% paraformaldehyde and either 0.5% glutaraldehyde in 0.1 M Millonig's phosphate buffer (pH 7.4). The brain was removed from the skull and placed in fresh fixative overnight at 4° C. Coronal sections (50-200 μm) were cut on an Oxford Vibratome (Lancer) and collected in serial order in 0.1 M phosphate buffer. After being osmicated (30 min in 1% $OsO_4$ in 0.1 M phosphate buffer) the sections were stained for 15 min in 0.1% uranyl acetate in sodium acetate buffer at 4° C., dehydrated in ethanols, cleared in propylene oxide and embedded in Araldite between two sheets of Melanex (ICI). Semi thin (1 μm) sections were cut with glass knives and stained with toluidine blue adjacent to thin sections cut with a diamond knife on a Reichert Ultracut ultramicrotome. The sections were collected on mesh grids coated with a thin formvar film, counterstained with lead citrate and viewed in a Jeol 1010 electron microscope. An electron micrograph of a NII from a 17 month old R6/5 homozygous mouse is shown in FIG. 6c. This NII (large arrow) contains high molecular weight fibrous structures which were clearly differentiated from the surrounding chromatin. The filaments were randomly oriented, 5-10 nm in diameter and often measured up to 250 nm in length (small arrows). These structures differ from those previously reported in the NIIs seen in hemizygous R6/2 mice which were far more granular in composition, with individual filamentous structures being more difficult to distinguish (Davies et al., 1997). R6/2 mice exhibit an earlier age of onset with a more rapid progression of the phenotype and do not survive beyond 13 weeks (Mangiarini et al., 1996). It is possible that the filamentous structures do not have time to form in the R6/2 mice.

EXAMPLE 5

Construction of Further Plasmids, Purification of Corresponding GST Fusion Proteins and Proleolytic Cleavage of GST Fusion Proteins In a second set of experiments, a further number of plasmids was constructed. Standard protocols for DNA manipulations were followed (J. Sambrook, E. F. Fritsch, and T. Maniatis, Molecular Cloning: A Laboratory Manual, 2nd Ed., Cold Spring Harbor Laboratory Press, Plainview, N.Y., 1989). IT-15 cDNA sequences (HDCRG, Cell 72, 971 (1993)) encoding the N-terminal portion of huntingtin, including the CAG repeats, were amplified by PCR using the oligonucleotides ES25 (5'-TGGGATCCGCATGGCGAC-CCTGGAAAAGCTGATGA AGG-3') (Seq. ID No. 1) and ES27 (3'-CTCCTCGAGCGGCGGTGGCGGCTGT-TGCTG CTGCTGCTG-5') (Seq. ID No. 3) as primers and the plasmids pCAG20 and pCAG51 as template (E. Scherzinger, R. Lurz, M. Trumaine, L. Margiarini, B. Hollenbach, R. Hasenbank, G. P. Bates, S. W. Davies, H. Lehrach, and E. E. Wanker, Cell 90, 549 (1997)). Conditions for PCR were as described (L. Mangiarini, K. Sathasivam, M. Seller, B. Cozens, A Harper, C. Hetherington, M. Lawton, Y Trottier, H. Lehrach, S. W. Davies, and G. P. Gates, Cell 87, 493 (1996)). The resulting cDNA fragments were gel purified, digested with Bam HI and Xho I and were inserted into the Bam HI-Xho I site of the expression vector pGEX-5X-1 (Pharmacia), yielding pCAG20DP and pCAG51DP, respectively. The plasmids pCAG20DP-Bio and pCAG51DP-Bio were generated by subcloning the PCR fragments obtained from the plasmids pCAG20 and pCAG51 into pGEX-5X-1-Bio. PGEX-5X-1-Bio was created by ligation of the oligonucleotides BIO1 (5'-CGCTCGAGGGTATCTTCGAGGCCCA-GAAGATCGAGTG GCGATCACCATGAG-3') (Seq. ID No. 4) and B102 (5'-GGCCGCTCATGGTGATCGCC ACTCGATCTTCTGGGCCTCGAAGATACCCTCGAG-3') (Seq. ID No. 5), after annealing and digestion with Xho I, into the Xho I-Not I site of pGEX-5X-1. The plasmids with the IT-15 cDNA inserts were sequenced to confirm that no errors had been introduced by PCR. The construction of plasmids pTL1-CAG20, pTL1-CAG51 and pTL1-CAG93 for the expression of huntingtin exon 1 proteins containing 20, 51 and 93 glutamines in mammalian cells has been described (A. Sittler, S. Walter, N. Wedemeyer, R. Hasenbank, E. Scherzinger, G. P. Bates, H. Lehrach, and E. E. Wanker, Mol. Cell, submitted).

Figure 8:
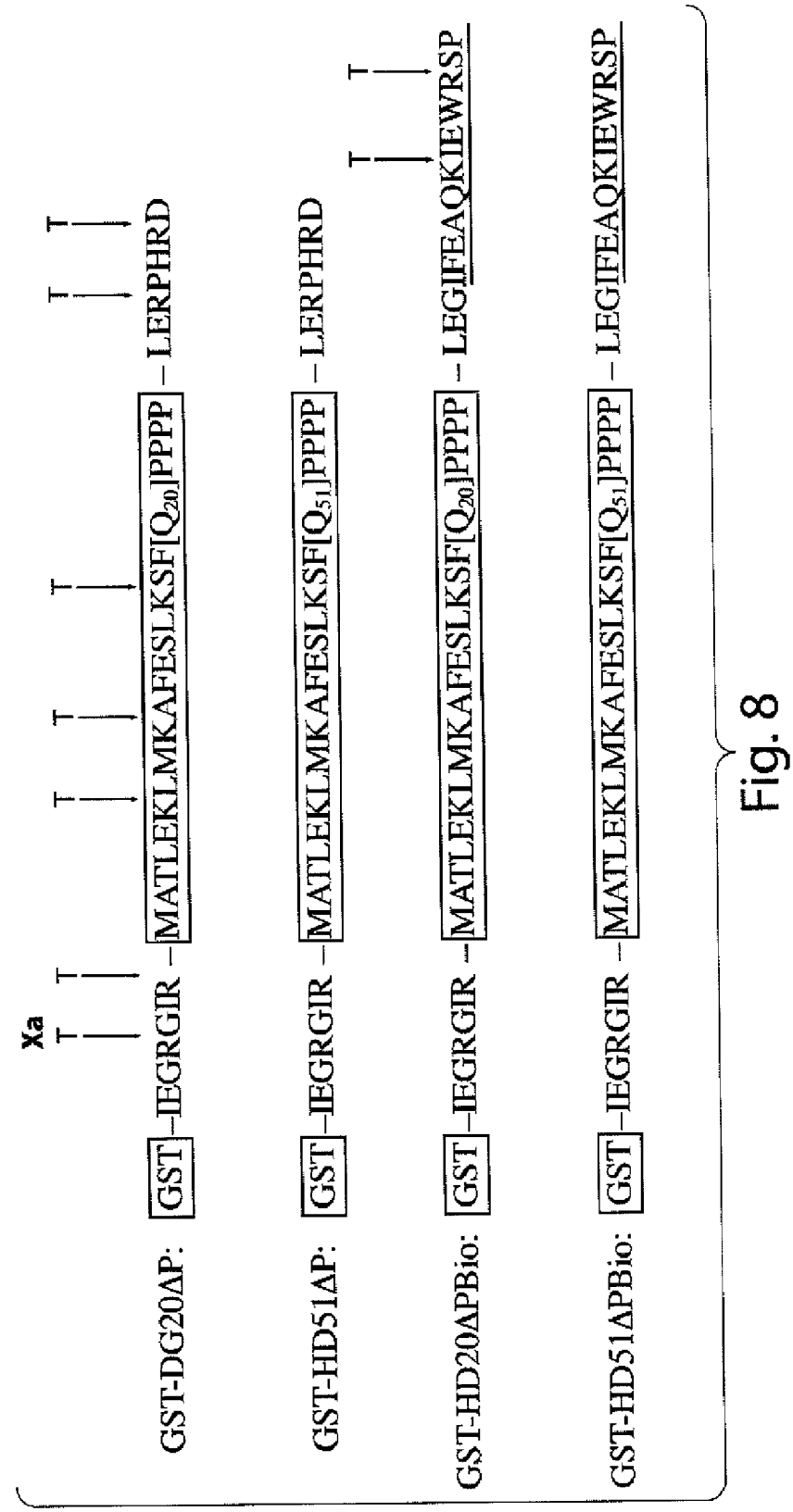

The amino acid sequence of the GST-HD fusion proteins encoded by the E. coli expression plasmids pCAG20DP, pCAG51DP, pCAG20Dp-Bio and pCAG51DP-Bio is shown in FIG. 8. The plasmids pCAG20DP and pCAG51DP encode fusion proteins of glutathione S-transferase (GST) and the N-terminal portion of huntingtin containing 20 (GST-HD20DP) and 51 (-HD5 IDP) polyglutamines, respectively. In these proteins the proline-rich region located immediately downstream of the glutamine repeat was deleted (E. Scherzinger, R. Lurz, M. Trumaine, L. Margiarini, B. Hollenbach, R. Hasenbank, G. P. Bates, S. W. Davies, H. Lehrach, and E. E. Wanker, Cell 90, 549 (1997). The fusion proteins GST-HD20DPBio and -HD51DPBio are identical to GST-HD20DP and -HD51DP, except for the presence of a biotinylation site (P. J. Schatz, Biotechnology 11, 1138 (1993)) at their C-termini.

In the experiments described herein, E. coli DH10B (BRL) was used for plasmid construction and E. coli SCSI (Stratagene) was used for the expression of GST-HD fusion proteins. Transformation of E. coli with plasmids and ligation mixtures was performed by electroporation using a Bio-Rad Gene Pulser (Richmond, Calif.). Transformed cells were spread on LB plates supplemented with appropriate antibiotics (J. Sambrook, E. F. Fritsch, and T. Maniatis, Molecular Clone: A Laboratory Manual, 2nd Ed., Cold Spring Harbor Laboratory Press, Plainview, N.Y. 1989). For expression of GST fusion proteins, cells were grown in liquid TY medium (5 g NaCl, 5 g yeast extract, and 10 g tryptone per liter) buffered with 20 mM MOPS/KOH (pH 7.9) and supplemented with glucose (0.2%), thiamine (20 µg/ml), ampicillin (100 µg/ml) and kanamycin (25 µg/ml).

The procedure for purification of GST fusion proteins is an adaption of the protocol of Smith and Johnson (D. B. Smith and K. S. Johnson, Gene 67, 31 (1988)). Unless indicated otherwise, all steps were performed at 0-4° C.

First, 100 ml TY medium were inoculated with a single colony containing the expression plasmid of interest, and the culture was incubated at 37° C. overnight with shaking. Then, 1.5 liter TY medium were inoculated with the overnight culture and grown at 37° C. until an $OD_{600}$ of 0.6 was reached. IPTG was added to a final concentration of 1 mM, and the culture continued to grow at 37° C. for 3.5 h with vigorous shaking. The culture was chilled on ice, and the cells harvested by centrifugation at 4000×g for 20 min.

Cells were washed with buffer A [50 mM sodium phosphate (pH 8), 150 mM NaCl, and 1 mM EDTA]. If necessary, the cell pellet was stored at -70° C. Cells were resuspended in 25 ml buffer A. PMSF and lysozyme (Boehringer Mannheim) were added to 1 mM and 0.5 mg/ml, respectively, and incubated on ice for 45 min. Cells were lysed by sonication (2×45 s, 1 min cooling, 200-300 Watt), and Triton X-100™ was added to a final concentration of 0.1% (v/v). The lysate was centrifuged at 30.000×g for 30 min, and the supernatant was collected.

5 ml of a 1:1 slurry GST-agarose (Sigma), previously-equilibrated in buffer A, was added and the mixture was stirred for 30 min. The slurry was poured into a 1.6 cm diameter column, washed once with 40 ml buffer A containing 1 mM PMSF and 0.1% Triton X-100™ and twice with 40 ml buffer A containing 1 mM PMSF. The protein was eluted with 5×2 ml buffer A containing 15 mM reduced glutathione (Sigma). Aliquots of the fractions were analyzed by SDS-PAGE and the fractions containing purified GST fusion protein were combined. Finally, the pooled fractions were dialysed overnight against buffer B [20 mM Tris/HCl (pH 8), 150 mM NaCl, 0.1 mM EDTA and 5% (v/v) glycerol], aliquoted, freezed in liquid nitrogen and stored at -70° C.

Typical yields were 10-20 mg for GST-HD20DP and -HD51DP and 5-10 mg for GST-HD20DPBio and -HD51 DPBio per liter of bacterial culture. Protein concentration was determined using the Coomassie protein assay reagent from Pierce with BSA as a standard.

The GST-huntingtin fusion proteins (2 mg) were digested with bovine factor Xa (New England Biolabs) or with modified trypsin (Boehringer Mannheim, sequencing grade) at an enzyme/substrate ratio of 1:10 (w/w) and 1:20 (w/w), respectively. The reaction was carried out in 20 µl of 20 mM Tris/HCl (pH 8), 150 mM NaCl and 2 mM $CaCl_2$. Incubations with factor Xa were performed at 25° C. for 16 h. Tryptic digestions were at 37° C. for 3 to 16 h. Digestions were terminated by the addition of 20 µl 4% (w/v) SDS and 100 mM DTT, followed by heating at 98° C. for 5 min.

As shown in the previous examples, removal of the GST tag from the HD exon 1 protein containing 51 glutamines (GST-HD51) by site-specific proteolytic cleavage results in the formation of high molecular weight protein aggregates, seen as characteristic fibrils or filaments on electron microscopic examination. Such ordered fibrillar structures were not detected after proteolysis of fusion proteins containing only 20 (GST-HD20) or 30 (GST-HD30) glutamines, although light scattering measurements (Y. Georgalis, E. B. Starikov, B. Hollenbach, R. Lurz, E. Scherzinger, W. Saenger, H. Lehrach, and E. E. Wanker, *Proc. Natl. Acad. Sci. USA* 95, 6118 (1998)) revealed that some form of aggregation also occurred with these normal repeat-length proteins. In the present example, truncated GST-HD exon 1 fusion proteins with or without a C-terminal biotinylation tag (P. J. Schatz, *Biotechnology* 11, 1138 (1993) were used. These fusion proteins contain either 20 or 51 glutamines but lack most of the proline rich region located downstream of the glutamine repeat (E. Scherzinger, R. Lurz, M. Trumaine, L. Margiarini, B. Hollenbach, R. Hasenbank, G. P. Bates, S. W. Davies, H. Lehrach, and E. E. Wanker, *Cell* 90, 549 (1997)). Potential factor Xa and trypsin cleavage sites within the GST-HD fusion proteins are shown in FIG. 8. As outlined above, the proteins GST-HD20DP and -HD51DP were expressed in *E. coli* and affinity-purified under native conditions. They were then digested overnight with trypsin or faxtor Xa protease to promote the formation of polyglutamine-containing huntingtin aggregates. FIG. 9A shows an immunoblot of a cellulose acetate membrane to which the native GST-HD20DP and -HD51DP proteins and their factor Xa and trypsin cleavage products have been applied.

Figure 10A:
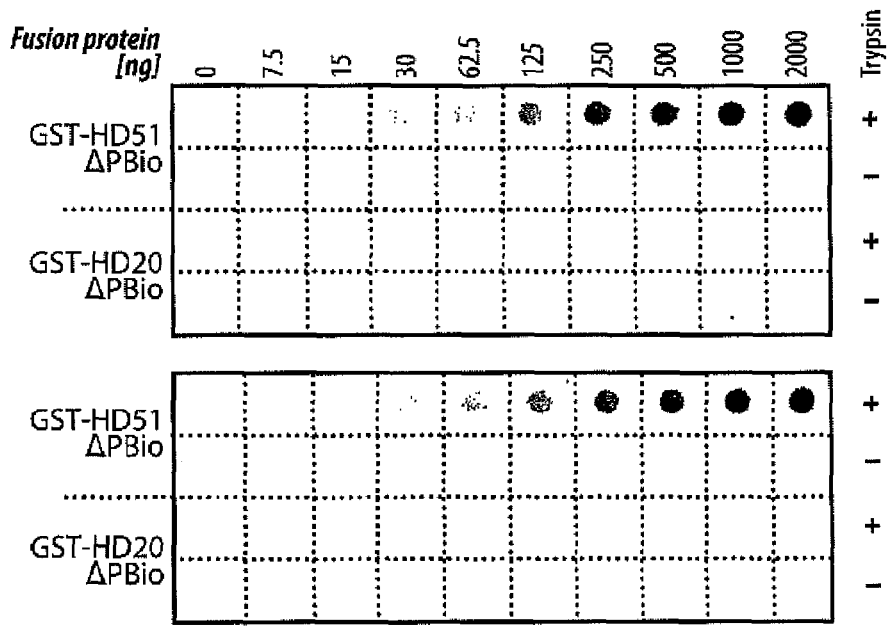
Figure 10B:
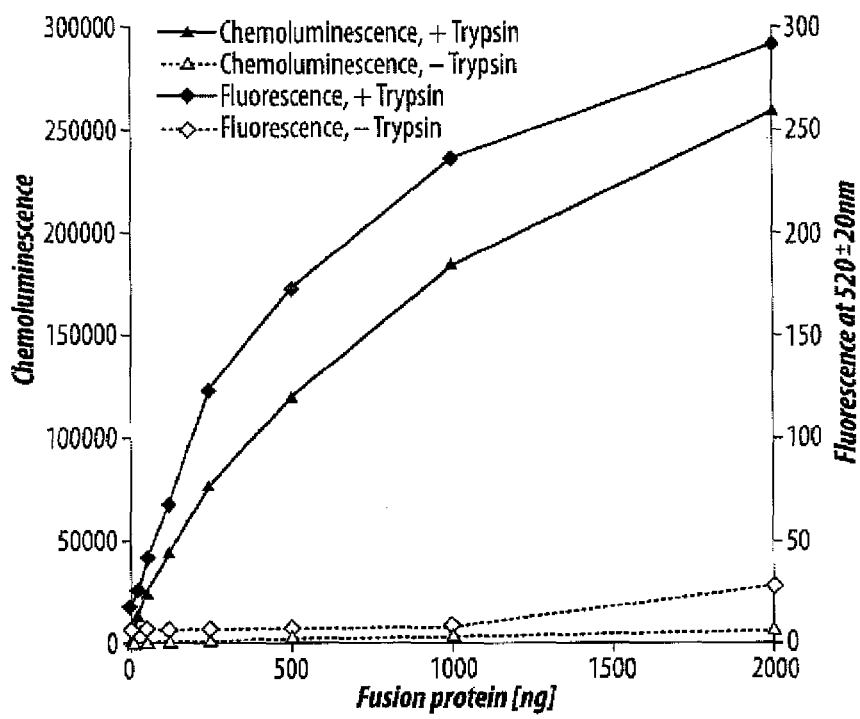

To monitor the in vitro formation of polyglutamine-containing aggregates without the need for a specific antibody, a modified filter retardation assay was developed. In this assay, streptavidin-conjugated alkaline phosphatase (AP) is used to detect the insoluble protein aggregates retained on the cellulose acetate filter membrane. Streptavidin binds specifically to the biotinylation tag (P. J. Schatz, *Biotechnology* 11, 1138 (1993)) that has been added C-terminal to the polyglutamine tract in the fusion proteins GST-HD20DPBio and -HD51DPBio (FIG. 7) (see Example 8 for details). FIG. 10A shows that the modified aggregation assay gives results comparable to those obtained with the non-biotinylated fusion proteins in that insoluble aggregates are produced from the trypsin-treated GST-HD51DPBio protein but not from the uncleaved GST-HD51DPBio protein or the corresponding 20 repeat samples. Using either fluorescent (AttoPhos™) or chemiluminescent (CDP-Star™) substrates for alkaline phosphatase, it is possible to capture and quantify the filter assay results with the Boehringer Lumi-Imager F1 system. With both AP substrates, aggregates formed from as little as 5-10 ng of input GST-HD51DPBio protein were readily detected on the cellulose acetate membrane, and signal intensities increased linearly up to 250 ng of fusion protein applied to the filter (FIG. 10B).

EXAMPLE 6

Isolation of Amyloid-Like Protein Aggregates from Transfected COS-1 Cells

To examine whether polyglutamine-containing aggregates are also formed in vivo, HD exon 1 proteins with 20, 51 or 93 glutamines (without a GST tag) were expressed in COS-1 cells. Whole cell lysates were prepared, and after centrifugation, the insoluble material was collected and treated with DNaseI and trypsin to lower the viscosity. The resulting protein mixture was then boiled in SDS and analyzed using the dot-blot filter retardation assay (see Example 8). In more detail, the following experimental protocol was carried out:

COS-1 cells were grown in Dulbecco's modified Eagle medium (Gibco BRL) supplemented with 5% (w/v) fetal calf serum (FCS) containing penicillin (5 U/ml) and streptomycin (5 µg/ml), and transfection was performed as described (A. Sittler, D. Devys, C. Weber, and J.-L. Mandel, *Hum. Mol. Genet.* 5, 95 (1996)).

COS-1 cells transfected with the mammalian expression plasmids pTL1-CAG20, pTL1-CAG51 and pTL1-CAG93 were harvested 48 h after transfection. The cells were washed in ice cold PBS, scraped and pelleted by centrifugation (2000×g, 10 min, 4° C.). Cells were lysed on ice for 30 min in 500 ml lysis buffer [50 mM Tris/HCl (pH 8.8), 100 mM NaCl, 5 mM $MgCl_2$, 0.5% (w/v) NP-40, 1 mM EDTA] containing the protease inhibitors PMSF (2 mM), leupeptin (10 µl/ml), pepstatin (10 µg/ml), aprotinin (1 µg/ml) and antipain (50 µg/ml). Insoluble material was removed by centrifugation for 5 min at 14000 rpm in a microfuge at 4° C. Pellets containing the insoluble material were resuspended in 100 ml DNase buffer [20 mM Tris/HCl (pH 8.0), 15 mM $MgCl_2$], and DNase I (Boehringer Mannheim) was added to a final concentration of 0.5 mg/ml followed by incubation at 37° C. for 1 h. After DNase treatment the protein concentration was determined by the Dot Metric assay (Geno Technology) using BSA as a standard. Eight µl 1 M Tris/HCl (pH 8.4), 1 µl 1% (w/v) SDS, 1 µl 0.2 M $CaCl_2$ and 10 µl trypsin (0.25 mg/ml) were then added, and the mixture was incubated for an additional 4 h at 37° C. Digestions were terminated by adjusting the mixtures to 20 mM EDTA, 2% (w/v) SDS and 50 mM DTT, followed by heating at 98° C. for 5 min.

FIG. 9C shows that insoluble protein aggregates are being formed in transfected COS cells expressing the HD exon 1 protein with 51 and 93 glutamines but not in COS cells expressing the normal exon 1 allele with 20 glutamines or in the non-transfected control cells. Thus, as observed in vitro with purified GST fusion proteins, formation of high molecular weight protein aggregates in vivo occurs in a repeat length-dependent way and requires a polyglutamine repeat in the pathological range. In addition, like the in vitro aggregates, the HD exon 1 aggregates formed in vivo are resistant to digestion with trypsin as well as to boiling in 2% (w/v) SDS.

EXAMPLE 7

Isolation of Amyloid-Like Protein Aggregates from Alzheimer's Disease Brain

It has been shown that the neurodegenerative disorder Alzheimer's disease (AD) is caused by the formation of β-amyloids and neurofibrillar tangles (NFTs) mainly occurring in the neocortex, hippocampus and amygdala (K. Beyreuther, and C. L. Masters, *Nature* 383, 476 (1996)). To determine whether these structures can be detected by the dot-blot filter retardation assay brain extracts of patients and controls were prepared and analyzed using the anti-Tau, anti-β-amyloid and anti-HD1 antibodies.

Figure 12:
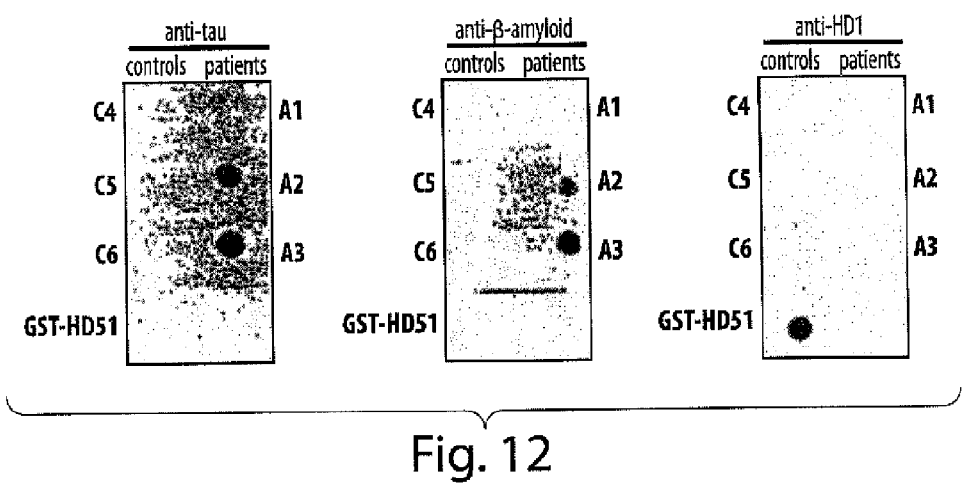

FIG. 12 shows that with the anti-Tau and anti-β-amyloid antibodies NFTs and β-amyloids were detected in brain extracts prepared from patients A2 and A3, but not in brain extracts prepared from patient A1 and the controls. Clinical studies revealed that the patients A2 and A3 had Alzheimer's disease with an intermediate and severe intellectual impairment, respectively, whereas patient A1 suffered only from moderate intellectual impairment. This indicates that the results obtained with the filter retardation assay correlate with the severity of the disease. Using the HD1 antibody in the brain extracts prepared from AD patients and controls no aggregated huntingtin protein was detected. However, the antibody reacted with the GST-HD51 protein which was used as a positive control.

Human cerebral cortex (~500 mg) was homogenized in 2.5 ml of lysis buffer (0.32 M sucrose, 1 mM $MgCl_2$, 5 mM $KH_2PO_4$, pH 7.0, 1 mM PMSF) using nine strokes of a glass homogenizer. The homogenate was centrifuged for 15 min at 500×g to remove the nuclei. The original supernatant was then centrifuged at 93500×g for 1 h yielding a membrane pellet. The pellet was dissolved in 2-5 ml 100 mM Tris-HCl (pH 8), 0.5% SDS and trypsin (Boehringer Mannheim, sequencing grade) was added to a final concentration of 0.05 mg/ml followed by incubation at 37° C. overnight. Digestions were terminated by adjusting the mixtures to 2% SDS and 50 mM DTT, followed by heating at 98° C. for 5 min. The mixture was centrifuged for 1 h at 110000×g and the resulting pellet was resuspended in 100 µl of water. Aliquots (2-10 µl) were then used for the analysis with the dot-blot filter retardation assay.

EXAMPLE 8

Dot-Blot Filter Retardation Assay

The filter assay used to detect polyglutamine-containing huntingtin protein aggregates has been described (hereinabove and in E. Scherzinger, R. Lurz, M. Trumaine, L. Margiarini, B. Hollenbach, R. Hasenbank, G. P. Bates, S. W. Davies, H. Lehrach, and E. E. Wanker, Cell 90, 549 (1997)). Denatured and reduced protein samples were prepared as described above, and aliquots corresponding to 50-250 ng fusion protein (GST-HD20DP and GST-HD51DP) or 5-30 µg extract protein (pellet fraction) were diluted into 200 µl 0.1% SDS and filtered on a BRL dot blot filtration unit through a cellulose acetate membrane (Schleicher and Schuell, 0.2 µm pore size) that had been preequilibrated with 0.1% SDS. Filters were washed 2 times with 200 µl 0.1% SDS and were then blocked in TBS (100 mM Tris/HCl, pH 7.4, 150 mM NaCl) containing 3% nonfat dried milk, followed by incubation with the anti-HD1 (1:1000) (see above and E. Scherzinger, R. Lurz, M. Trumaine, L. Margiarini, B. Hollenbach, R. Hasenbank, G. P. Bates, S. W. Davies, H. Lehrach, and E. E. Wanker, Cell 90, 549 (1997), the anti-Tau (Dako, 1:1000) or the anti-β-amyloid antibody (Dako, 1:300). The filters were washed several times in TBS, then incubated with a secondary anti-rabbit or anti-mouse antibody conjugated to horseraddish peroxidase (Sigma, 1:5000) followed by ECL (Amersham) detection. The developed blots were exposed for various times to Kodak X-OMAT film or to a Lumi-Imager (Boehringer Mannheim) to enable quantification of the immunoblots.

For detection and quantification of polyglutamine-containing aggregates generated from the protease-treated fusion proteins GST-HD20DPBio and -HD51DPBio, the biotin/streptavidin-AP detection system was used. Following filtration, the cellulose acetate membranes were incubated with 1% (w/v) BSA in TBS for 1 h at room temperature with gentle agitation on a reciprocal shaker. Membranes were then incubated for 30 min with streptavidin-alkaline phosphatase (Promega) at a 1:1000 dilution in TBS containing 1% BSA, washed 3 times in TBS containing 0.1% (v/v) Tween 20 and 3 times in TBS, and finally incubated for 3 min with either the fluorescent alkaline phosphatase substrate AttoPhOs™ or the chloro-substituted 1,2-dioxetane chemiluminescence substrate CDP-Star™ (Boehringer Mannheim) in 100 mM Tris/HCl, pH 9.0, 100 mM NaCl and 1 mM $MgCl_2$. Fluorescent and chemiluminescent signals were imaged and quantified with the Boehringer Lumi-Imager F1 system and LumiAnalyst™ software (Boehringer Mannheim).

EXAMPLE 9

Microtitre Plate Filter Retardation Assay

To process a large number of proteolytic digestion reactions in parallel, a microtitre plate filter retardation assay was developed. In this assay a 96-well microtitre plate containing a cellulose acetate membrane with a pore size of 0.45 mm (Whatman Polyfiltronics) was used for the retention of polyglutamine-containing protein aggregates.

The following experimental protocol was employed:

First, 15 µl GST fusion protein solution (200 µg/ml GST-HD51DPBio or GST-HD20DPBio in buffer P [20 mM Tris/HCl (pH 8.0), 150 mM NaCl]) and 15 µl trypsin solution (10 µg/ml trypsin (Boehringer Mannheim, sequencing grade) in buffer P) were combined in a 96-well Thermo-Fast®96 tube plate (Advanced Biotechnologies LTD) using a multi channel pipette (Eppendorf), and the microtitre plate was incubated for 16 hours at 37° C. Then 30 µl SDS/DTT solution (4% SDS, 100 mM DTT in buffer P) were added to each well, the plate was sealed with a microtitre plate sealer (Biostat LTD) and the plate was heated in a 96-well MasterCycler (Eppendorf-Netheler-Hinz) for 5 min at 98° C.

The sealing was removed and 50 µl of the reaction mix were transferred into each well of a new 96-well microtitre plate containing a 0.45 µm cellulose acetate membrane, pre-equilibrated with 0.1% (w/v) SDS, using a multi channel pipette. For equilibration of the cellulose acetate membrane, the microtitre plate was placed into the QIAvac Manifold-96 (Qiagen) and 200 µl 0.1% SDS was pipetted into each well of the plate. Vacuum was then applied until the SDS solution had passed through the filter. Prior to addition of the protein solution, each well of the filter plate was preloaded with an additional 200 µl of 0.1% SDS. The diluted protein solution was then filtered through the membrane by applying vacuum.

The filterplate was washed with 2×200 µl 0.1% SDS and 2×200 ml TBS (100 mM Tris/HCl (pH 7.4), 150 mM NaCl). Vacuum was used to remove wash solutions from the membrane. 200 µl 0.2% (w/v) BSA in TBS were pipetted into each well of the filterplate, and the plate was incubated for 1 h at room temperature (RT) (blocking). Blocking buffer was removed by pipetting.

Next, 200 µl streptavidin alkaline phosphatase (1:1000, Promega) in 0.2% (w/v) BSA/TBS were added to each sample, and the filterplate was incubated for 1 h at RT. Streptavidin AP buffer was removed by pipetting. The filterplate was washed with 3×200 µl TTBS [100 mM Tris/HCl (pH 7.4), 150 mM NaCl, 0.1% (v/v) Tween 20] and 3×200 µl TBS. Vacuum was used to remove wash solutions.

200 μl detection buffer (50 mM Tris/HCl (pH 9.0), 500 mM NaCl, 1 mM Mg C12) were added to each sample, incubated for 1 min and vacuum was applied to remove the buffer. 200 μl Attophos™ (10 mM AttoPhos™) in detection buffer were pipetted into each well of the filterplate, incubated for 1 h at RT, vacuum was applied to remove the buffer, and the fluorescence emission of each well was measured with the CytoFluor®4000 (Perseptive Biosystems) at 485+/−20 (excitation) and 530+/−25 (emission). Finally, the resultant images were analysed with CytoFluor 4.1 software and MS Excel 7.0.

As expected from the text set of experiments, using fusions of GST and the full-length HD exon 1 protein, only the cleavage products of GST-HD51DP were retained by the filter and were detected by the huntingtin-specific antibody HD1, indicating the formation of high molecular weight HD51DP aggregates from this fusion protein. Scanning electron microscopy of the material retained on the surface of the membrane revealed bunches of long fibrils or filaments (FIG. 9B), which were not detected after filtration of the uncleaved GST-HD51DP preparation or the protease-treated GST-HD20DP preparation. These results indicate that an elongated polyglutamine sequence but not the proline rich region in the HD exon 1 protein is necessary for the formation of high molecular weight protein aggregates in vitro.

Figure 11A:
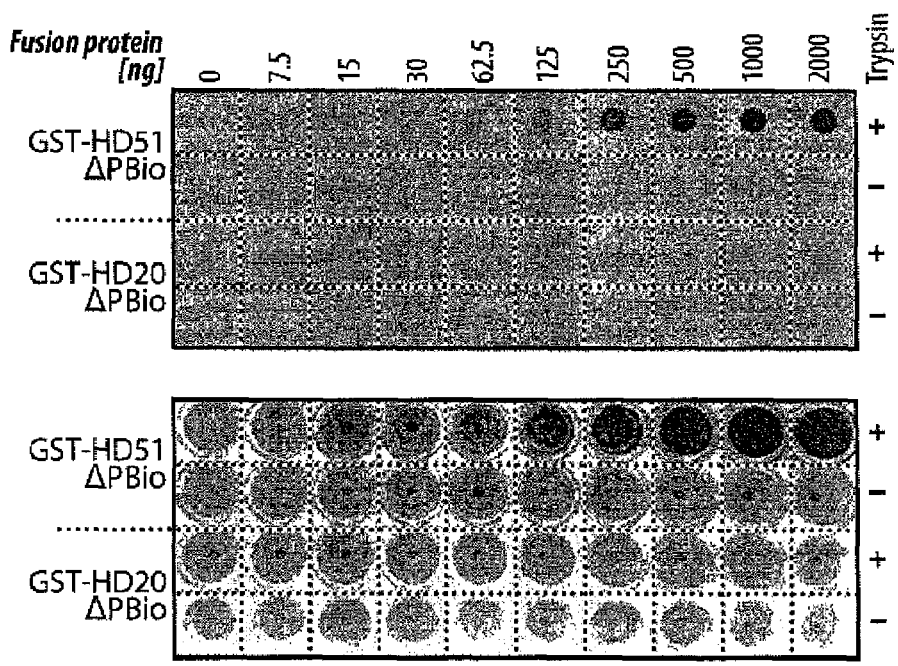
Figure 11B:
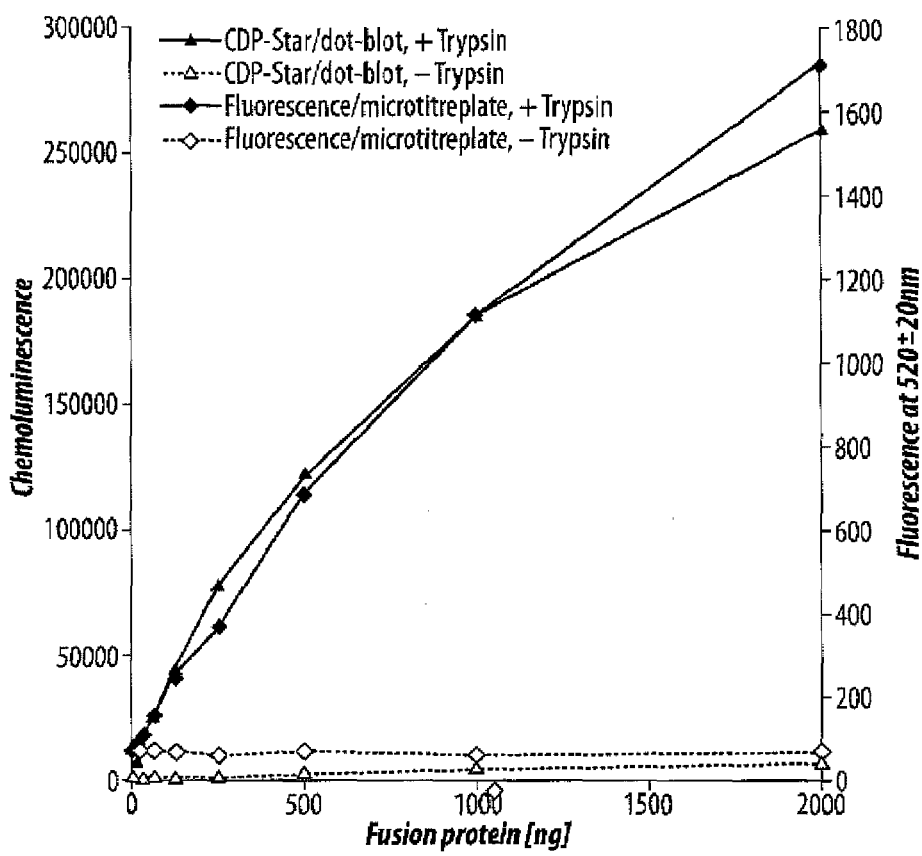

Essentially, the same results as with the dot blot filter retardation assay were obtained when the fusion proteins GST-HD20DPBio and -HD51DPBio were analysed with the microtitre plate filter retardation assay, indicating that this assay can be used for the high throughput isolation of chemical compounds from chemical libraries (FIGS. 11A and B).

REFERENCES

Bates, G. P., Mangiarini, L., Mahal, A. and Davies, S. W. (1997). Transgenic models of Huntingtons disease. Hum. Mol. Genet. 6, 1633-1637.

Booth, D. R., Stunde, M., Bellotti, V., Robinson, C. V., Hutchinson, W. L., Fraser, P. E., Hawkins, P. N., Dobson, C. M., Radford, S. E., Blake, C. C. F., and Pepys, M. B. (1997). Instability, unfolding and aggregation of human lysozyme variants underlying amyloid fibrillogenesis. Nature 385, 787-793.

Burke, J. R., Enghild, J. J., Martin, M. E., Jou, Y.-S., Myers, R. M., Roses, A. D., Vance, J. M., and Strittmatter, W. J. (1996). Huntingtin and DRPLA proteins selectively interact with the enzyme GAPDH. Nature Med. 2, 347-350.

Caputo, C. B., Fraser, P. E., Sobel, I. E., and Krischner, D. A. (1992). Amyloid-like properties of a synthetic peptide corresponding to the carboxy terminus of b-amyloid protein precursor. Arch. Bioch. Biophys. 292, 199-205.

Caughey, B., and Chesebro, B. (1997). Prion protein and the transmissible spongiform encephalopathies. Trends Cell Biol. 7, 56-62.

Davies, S. W., Trumaine, M., Cozens, B. A., DiFiglia, M., Sharp, A. H., Ross, C. A., Scherzinger, E., Wanker, E. E., Mangiarini, L., and Bates, G. P. (1997). Formation of neuronal intranuclear inclusions (NII) underlies the neurological dysfunction in mice transgenic for the HD mutation. Cell 90, 537-548.

de Rooij, K. E., Dorsman, J. C., Smoor, M. A., T., d. D. J., and van Ommen, G.-J. (1996). Subcellular localisation of the Huntington's disease gene product in cell lines by immunofluorescence and biochemical subcellular fractionation. Hum. Mol. Genet. 5, 1093-1099.

DiFiglia, M., Sapp, E., Chase, K., Schwarz, C., Meloni, A., Young, C., Martin, E., Vonstattel, J.-P., Carraway, R., Reeves, S. A., Boyce, F. M., and Aronin, N. (1995). Huntingtin is a cytoplasmic protein associated with vesicles in human and rat brain neurons. Neuron 14, 1075-1081.

Duyao, M. P., Auerbach, A. A., Ryan, A., Persichetti, F., Barnes, G. T., McNeil, S. M., Ge, P., Vonstattel, J.-P., Gusella, J. F., Joyner, A. L., and MacDonald, M. E. (1995). Inactivation of the mouse Huntington's disease gene homolog Hdh. Science 269, 407-410.

Glenner, G. G. (1980). Amyloid deposits and amyloidosis. N. Engl. J. Med. 302, 1283-1292, 1333-1343.

Goldberg, Y. P., Nicholson, D. W., Rasper, D. M., Kalchman, M. A., Koide, H. B., Graham, R. K., Bromm, M., Kazemi-Esfarjani, P., Thornberry, N. A., Vaillancourt, J. P., and Hayden, M. R. (1996). Cleavage of huntingtin by apopain, a proapoptotic cysteine protease, is modulated by the polyglutamine tract. Nature Genet. 13, 442-449.

Gutekunst, C.-A., Levey, A. I., Heilman, C. J., Whaley, W. L., Yi, H., Nash, N. R., Rees, H. D., Madden, J. J., and Hersch, S. M. (1995). Identification and localization of huntingtin in brain and human lymphoblastoid cell lines with antifusion protein antibodies. Proc. Natl. Acad. Sci. USA 92, 8710-8714.

Harper, P. S. (1991). Huntington's disease, 22 Edition, P. S. Harper, ed. (London: W.B. Saunders Co, Ltd).

HDCRG (1993). A novel gene containing a trinucleotide repeat that is unstable on Huntington's disease chromosomes. Cell 72, 971-983.

Hoogeveen, A. T., Willemsen, R., Meyer, N., de Rooij, K. E., Roos, R. A. C., van Ommen, G.-J. B., and Galjaard, H. (1993). Characterisation and localisation of the Huntington disease gene product. Hum. Mol. Genet. 2, 2069-2073.

Ikeda, H., Yamaguchi, M., Sugai, S., Aze, Y., Narumiya, S., and Kakizuka, A. (1996). Expanded polyglutamine in the Machado-Joseph disease protein induces cell death in vitro and in vivo. Nature Genet. 13, 196-202.

Jarrett, J. T., and Lansburry, P. T. (1993). Seeding "one-dimensional crystallization" of amyloid: a pathogenic mechanism in Alzheimer's disease and scrapie? Cell 73, 1055-1058.

Kalchman, M. A., Graham, R. K., Xia, G., Koide, H. B., Hodgson, J. G., Graham, K. C., Goldberg, Y. P., Gietz, R. D., Pickart, C. M., and Hayden, M. R. (1996). Huntingtin is ubiquinated and interacts with a specific ubiquitin-conjugating enzyme. J. Biol. Chem. 271, 19385-19394.

Kalchman, M. A., Koide, H. B., McCutcheon, K., Graham, R. K., Nichol, K., Nishiyama, K., Kazemi-Esfariani, P., Lynn, F. C., Wellington, C., Metzler, M., Goldberg, Y. P., Kanazawa, I., Gietz, R. D., and Hayden, M. R. (1997). *HIP*1, a human homologue of *S. cerevisiae* Sla2p, interacts with membrane-associated huntingtin in the brain. Nature Genet. 16, 44-53.

Li, X.-J., Li, S.-H., Sharp, A. H., Nucifora, F. C., Schilling, G., Lanahan, A., Worley, P., Snyder, S. H., and Ross, C. A. (1995). A huntingtin-associated protein enriched in brain with implications for pathology. Nature 378, 398-402.

Lim, K., Ho, J. X., Keeling, K., Gilliland, G. L., J I, X., Rüker, F., and Carter, D. C. (1994). Three-dimensional structure of *Schistosoma japonicum* glutamine S-transferase fused with a six-amino acid conserved neutralizing epitope of gp41 from HIV. Prot. Sci. 3, 2233-2244.

Mangiarini, L., Sathasivam, K., Seller, M., Cozens, B., Harper, A., Hetherington, C., Lawton, M., Trottier, Y., Lehrach, H., Davies, S. W., and Bates, G. P. (1996). Exon 1 of the Huntington's disease gene containing a highly expanded CAG repeat is sufficient to cause a progressive neurological phenotype in transgenic mice. Cell 87, 493-506.

Onodera, O., Roses, A. D., Tsuji, S., Vance, J. M., Stritmatter, W. J., and Burke, J. R. (1996). Toxicity of expanded polyglutamine-domain proteins in *Escherichia coli*. FEBS Lett. 399, 135-139.

Perutz, M. F. (1996). Gulutamine repeats and inherited neurodegenerative diseases: molecular aspects. Curr. Opin. Struct. Biol. 6, 848-858.

Perutz, M. F., Johnston, T., Suzuki, M., and Finch, J. T. (1994). Glutamine repeats as polar zippers: their possible role in neurodegenerative diseases. Proc. Natl. Acad. Sci. USA 91, 5355-5358.

Portera-Cailliau, C., Hedreen, J. C., Price, D. L., and Koliatsos, V. E. (1995). Evidence of apoptotic cell death in Huntington disease and excitotoxic animal models. J. Neurosci. 15, 3775-3787.

Prusiner, S. B., Kinley, M. P. M., Bowman, K. A., Bolton, D. C., Bendheim, P. E., Groth, D. F., and Glenner, G. G. (1983). Scrapie prions aggregate to form amyloid-like birefingent rods. Cell 35, 349-358.

Roizin, L., Stellar, S., and Liu, J. C. (1979). Neuronal nuclear-cytoplasmic changes in Huntington's Chorea: Electron microcope investigations. Adv. Neurol. 23, 95-122.

Roos, R. A. C., and Bots, G. T. A. M. (1983). Nuclear membrane indentations in Huntington's chorea. J. Neurol. Sci. 61, 37-47.

Ross, C. A. (1995). When more is less: pathogenesis of glutamine repeat neurodegenerative diseases. Neuron 15, 493-496.

Rubinsztein, D. C., Leggo, J., Coles, R., Almqvist, E., Biancalana, V., Cassiman, J.-J., Chotai, K., Connarty, M., Crauford, D., Curtis, A., Curtis, D., Davidson, M. J., Differ, A.-M., Dode, C., Dodge, A., Frontali, M., Ranen, N. G., Stine, O. C., Sherr, M., Abbott, M. H., Franz, M. L., Graham, C. A., Harper, P. S., Hedreen, J. C., Jackson, A., Kaplan, J.-C., Losekoot, M., MacMillan, J. C., Morrison, P., Trottier, Y., Novelletto, A., Simpson, S. A., Theilmann, J., Whittaker, J. L., Folstein, S. E., Ross, C. A., and Hayden, M. R. (1996). Phenotypic characterisation Df individuals with 3040 CAG repeats in the Huntington's disease (HD) gene reveals HD cases with 36 repeats and apparently normal elderly individuals with 36-39 repeats. Am. J. Hum. Genet. 59, 16-22.

Sathasivam, K., Amaechi, I., Mangiarini, L., and Bates, G. P. (1997). Identification of an HD patient with a (CAG) 180 repeat expansion and the propagation of highly expanded CAG repeats in lambda phage. Hum Genet. 99, 692-695.

Sharp, A. H., Loev, S. J., Schilling, G., Li, S.-H., Li, X.-J., Bao, J., Wagster, M. V., Kotzuk, J. A., Steiner, J. P., Lo, A., Hedreen, J., Sisodia, S., Snyder, S. H., Dawson, T. M., Ryugo, D. K., and Ross, C. A. (1995). Widespread (expression of Huntington's disease gene (IT15) protein product. Neuron 14, 1065-1074.

Smith, D. B., and Johnson, K. S. (1988). Single-step purification of peptides expressed in *Eschedrichia coli* as fusions with glutathione S-transferase. Gene 67, 31-40.

Stott, K., Blackgurn, J. M., Butler, P. J. G., and Perutz, M. (1995). Incorporation of glutamine repeats makes protein oligomerize: implications for neurodegenerative diseases. Proc. Natl. Acad. Sci. USA 92, 6509-6513.

Tellez-Nagel, I., Johnson, B., and Terry, R. D. (1974). Studies on brain biopsies of patients with Huntington's chorea. J. Neurocyt. 3, 308-332.

Towbin, H., Staehelin, T., and Gordon, J. (1979). Electrophoretic transfer of proteins from polyacrylamide gels to nitrocellulose sheets: procedure and some applications. Proc. Natl. Acad. Sci. USA 76, 4350-4354.

Trottier, Y., Devys, D., Imbert, G., Sandou, F., An, I., Lutz, Y., Weber, C., Agid, Y., Hirsch, E. C., and Mandel, J.-L. (1995a). Cellular localisation of the Huntington's disease protein and discrimination of the normal and mutated forms. Nature Genet. 10, 104-110.

Trottier, Y., Lutz, Y., Stevanin, G., Imbert, G., Devys, D., Cancel, G., Sandou, F., Weber, C. David, G., Tora, L., Agid, Y., Brice, Al., and Mandel, J.-L. (1995b). Polyglutamine expansion as a pathological epitope in Huntington's disease and four dominant cerebellar ataxias. Nature, 378, 403-406.

Vonsattel, J.-P, Myers, R. H., Stevens, T. J., Ferrante, R. J., Bird, E. D., and Richardson, E. P. (1985). Neuropathological classification of Huntington's disease. J. Neuropath. Exap. Neurol. 44, 559-577.

Wanker, E. E., Rovira, C., Scherzinger, E., Hasenbank, R., Walter, S., Tait, D., Colicelli, J., and Lehrach, H. (197). HIP-1: A huntingtin interacting protein isolated by the yeast two-hybrid system. Hum. Mol. Genet. 6, 487-495.

We claim:

1. A method of detecting the presence of detergent- or urea-insoluble amyloid-like fibrils or protein aggregates in a sample on a filter comprising the following steps:
   (a) treating a sample suspected of comprising amyloid-like fibrils or protein aggregates by adding detergent or urea to solubilize the sample;
   (b) contacting a cellulose acetate or nitrocellulose filter having a pore size capable of retaining detergent- or urea-insoluble amyloid-like fibrils or protein aggregates with the sample and filtering said sample through the filter to capture said detergent or urea insoluble amyloid-like fibrils or protein aggregates; and
   (c) detecting said amyloid-like fibrils or protein aggregates that are retained on said filter.

2. The method of claim 1 wherein said amyloid-like fibrils or protein aggregates are indicative of a disease.

3. The method of claim 2 wherein said disease is a human disease.

4. The method of claim 2 wherein said disease is associated with a polyglutamine expansion.

5. The method of any one of claims 2 to 3 wherein said disease is Huntington's disease; spinal and bulbar muscular atrophy; dentarorubral pallidoluysian atrophy; spinocerebellar ataxia type-1, -2, -3, -6 or -7 Alzheimer disease; bovine spongiform encephalopathy (BSE); primary systemic amyloidosis; secondary systemic amyloidosis; senile systemic amyloidosis; familial amyloid polyneuropathy I; hereditary cerebral amyloid angiopathy; hemodialysis-related amyloidosis; familial amyloid polyneuropathy III; Finnish hereditary systemic amyloidosis; type II diabetes; medullary carcinoma of the thyroid; spongiform encephalopathies: Kuru, Gerstmann-Sträussler-Scheinker syndrome (GSS), familial insomnia, and scrapie; atrial amyloidosis; hereditary non-neuropathic systemic amyloidosis; injection-localized amyloidosis; hereditary renal amyloidosis; or Parkinson's disease.

6. The method of any one of claims 1 to 3 wherein, prior to step (c), the following step is carried out: (c') washing said filter so as to remove detergent- or urea-soluble material of the sample.

7. The method of any one of claims 1 to 3 wherein detergent- or urea-soluble material of the sample is simultaneously with or subsequent to the contacting of said filter with the sample in step (b), sucked through said filter.

8. The method of any one of claims 1 to 3 wherein detection in step (c) is effected by an antibody, or peptide or polypeptide, a tag or an enzyme, or a fragment or derivative thereof or a chemical reagent that specifically binds to said fibrils or aggregates.

9. The method of any one of claims 1 to 3 wherein detection in step (c) is performed by electron microscopy, electron scanning microscopy, fluorescence and/or chemiluminescence.

10. The method of claim 1 wherein the sample is derived from tissues or cells of bacteria, yeast, fungi, plants, insects or animals.

11. The method of claim 10 wherein said tissues or cells are from mammals, humans, a transgenic animal or a transgenic plant.

12. A method of detecting the presence of detergent- or urea-insoluble amyloid-like fibrils or protein aggregates in a sample on a filter comprising the following steps:
 (a) contacting a cellulose acetate or nitrocellulose filter having a pore size capable of retaining detergent- or urea-insoluble amyloid-like fibrils or protein aggregates with a sample suspected to comprise said amyloid-like fibrils or aggregates which has been previously treated with detergent or urea to solubilize the sample and filtering said sample through the filter to capture said detergent or urea-insoluble amyloid-like fibrils or protein aggregates; and
 (b) detecting said amyloid-like fibrils or protein aggregates that are retained the sample comprises a fusion protein comprising a peptide or polypeptide that enhances solubility or prevents aggregation of said fusion protein, an amyloidogenic peptide or polypeptide and a cleavable site that separates the above-mentioned components of the fusion protein, the method further comprising the following steps prior to step (a):
 (a') incubating said fusion protein in the presence of a suspected inhibitor of amyloid-like fibril or protein aggregate formation; and
 (a") simultaneously with or after step (a'), further incubating with a compound that induces cleavage at said cleavage site.

13. The method of claim 12 wherein said cleavable site is an enzymatically cleavable site or a chemically cleavable site or a site cleavable by intein self-cleavage in the presence of thiols.

14. The method of claim 12 further comprising, prior to step (b) and after step (a"):
 (a''') incubation with an inhibitor of said compound that induces cleavage.

15. The method of claim 12 wherein said amyloidogenic peptide or polypeptide comprises a polyglutamine expansion.

16. The method of one of claims 4 and 15 wherein said polyglutamine expansion comprises at least 35 glutamines.

17. The method of one of claims 4 and 15 wherein said polyglutamine expansion comprises at least 41 glutamines.

18. The method of one of claims 4 and 15 wherein said polyglutamine expansion comprises at least 48 glutamines.

19. The method of one of claims 4 and 15 wherein said polyglutamine expansion comprises at least 51 glutamines.

20. The method of any one of claims 1 and 12 wherein said contacting is effected by dotting, the sample onto said filter.

21. The method of any one of claims 1 and 12 wherein said filter is a filter membrane.

22. The method of any one of claims 1 and 12 wherein said detergent is Sodium Dodecyl Sulphate (SDS) or t-octylphenoxypolyethoxyethanol (TRITON X-100™).

23. The method of claim 12, wherein the compound is an enzyme.

24. The method of claim 23, wherein the enzyme is a protease.

25. The method of claim 12 wherein said amyloid-like fibrils or protein aggregates are indicative of a disease.

26. The method of claim 25 wherein said disease is a human disease.

27. The method of claim 25 wherein said disease is associated with a polyglutamine expansion.

28. The method of claim 25 wherein said disease is Huntington's disease; spinal and bulbar muscular atrophy; dentarorubral pallidoluysian atrophy; spinocerebellar ataxia type-1, -2, -3, -6 or -7; Alzheimer disease; bovine spongiform encephalopathy (B SE); primary systemic amyloidosis; secondary systemic amyloidosis; senile systemic amyloidosis; familial amyloid polyneuropathy I; hereditary cerebral amyloid angiopathy; hemodialysis-related amyloidosis; familial amyloid polyneuropathy III; Finnish hereditary systemic amyloidosis; type II diabetes; medullary carcinoma of the thyroid; spongiform encephalopathies: Kuru, Gerstmann-Sträussler-Scheinker syndrome (GSS), familial insomnia, and scrapie; atrial amyloidosis; hereditary non-neuropathic systemic amyloidosis; injection-localized amyloidosis; hereditary renal amyloidosis; or Parkinson's disease.

29. The method of claim 12 wherein said filter with low protein adsorption is cellulose acetate.

30. The method of claim 12 wherein, prior to step (b), the following step is carried out: (b') washing said filter so as to remove detergent- or urea-soluble material of the sample.

31. The method of claim 12 wherein detergent- or urea-soluble material of the sample is simultaneously with or subsequent to the contacting of said filter with the sample in step (a), sucked through said filter.

32. The method of claim 12 wherein detection in step (b) is effected by an antibody, a tag or an enzyme, or a fragment or derivative thereof or a chemical reagent that specifically binds to said fibrils or aggregates.

33. The method of claim 12 wherein detection in step (b) is performed by electron microscopy, electron scanning microscopy, fluorescence and/or chemiluminescence.

* * * * *